US006200981B1

(12) United States Patent
Kindon et al.

(10) Patent No.: US 6,200,981 B1
(45) Date of Patent: Mar. 13, 2001

(54) PYRIMIDIN DERIVATIVES

(75) Inventors: Nicholas Kindon, Ashby de la Zouch; Premji Meghani; Stephen Thom, both of Loughborough, all of (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 09/155,091
(22) PCT Filed: Jul. 15, 1998
(86) PCT No.: PCT/SE98/01391
   § 371 Date: Sep. 21, 1999
   § 102(e) Date: Sep. 21, 1999
(87) PCT Pub. No.: WO99/05123

PCT Pub. Date: Feb. 4, 1999

(30) Foreign Application Priority Data

Jul. 24, 1997 (SE) .................................................. 9702794

(51) Int. Cl.[7] ....................... A61K 31/505; C07D 239/10
(52) U.S. Cl. ............................................. 514/269; 544/294
(58) Field of Search ............................. 544/294; 514/269

Primary Examiner—Allen J. Robinson
Assistant Examiner—Barbara Badio
(74) Attorney, Agent, or Firm—Nixon & Vanderhye

(57) ABSTRACT

The invention relates to new pharmaceutically active compounds which are are P2-purinoceptor 7-transmembrane (TM) G-protein coupled receptor antagonists, compositions containing them and processes for their preparation.

11 Claims, No Drawings

PYRIMIDIN DERIVATIVES

This application is a 371 of PCT/SE98/01391 filed Jul. 15, 1998.

The invention provides new pharmaceutically active compounds, composition containing them and processes for their preparation. The compounds are useful in therapy because they are P2-purinoceptor 7-transmembrane (TM) G-protein coupled receptor antagonists.

ATP receptors have been shown to be present on a wide number of different cell types (Dubyak et al Am J Physiol (1993) 265, C577–C606). Neutrophils, monocytes and macrophages have been isolated from several species including humans and ATP and/or UTP have been shown to increase intracellular calcium levels. Activation of these receptors on leukocytes can either directly stimulate certain types of inflammatory response or can prime the effector cells to other inflammatory mediators in vivo. ATP can upregulate the expression of adhesion molecules (Freyer et al J Immun. (1988) 141, 580–586) which causes enhanced adhesion of circulating leukocytes to endothelial cells and their enhanced migration into the tissue space. ATP has also been shown to promote chemotaxis of both eutrophils and eosinophils (Verghese et al J. B. C. (1996) 271, 15597–15601 and Burders et al Blood (1993) 81, 49–55) which may promote an inflammatory response. ATP priming of neutrophils can also potentiate superoxide production (Seifert et al Eur J Biochem (1989) 181, 277–285). ATP receptors are also present on a number of other cell types such as chondrocytes, keratinocytes, microglia and goblet cells (Leong et al BBA (1994) 1201, 298–304; Pillai et al J Clin Invest (1992) 90, 42–51; Walz et al J Neuroscience (1993) 13, 4403–4411 and Abdullah et al Biochem J (1996) 316, 943–951). Stimulation of the receptors on these cells can stimulate or enhance inflammatory responses and antagonist of the receptor may therefore be of use in a number of inflammatory diseases such as asthma, inflammatory bowel disease, ARDS, psoriasis, rheumatoid arthritis, myocardial ischaemia, COPD, cystic fibrosis, arthereosclerosis, restenosis, peridontal disease, septic shock, osteoarthritis and stroke. ATP receptors have also been reported on tumour cells (Dubyak et al J. Biol. Chem., (1985) 260, 10653–10661 and Wagner et al Gastroenterolgy, (1997), 112(4) suppl. page A1198) and may be involved in the development of cancer. Antagonists may therefore be useful in treatment of cancer.

According to the invention there is provided a compound of formula (I) or salts thereof:

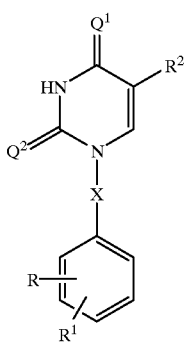

(I)

in which:

X is a bond, $CH_2$ or a $C_{1-3}$alkylene group optionally interrupted by oxygen;

R is hydrogen, $NO_2$, $NH_2$, $N(C_{1-6}alkyl)_2$, $CO_2H$, $CH_2OH$, halogen, $CO_2C_{1-6}alkyl$, $C_{1-8}alkyl$ optionally interrupted by one or more oxygen, nitrogen or sulphur atoms and optionally substituted by $CO_2H$, or R is hydroxy, phenyl optionally substituted by $CH_2CO_2H$, or $CONR^3R^4$ where $R^3$ and $R^4$ are independently hydrogen, $C_{1-6}alkyl$ optionally substituted by hydroxy or $CO_2H$ and/or optionally interrupted by oxygen, nitrogen or sulphur;

$R^1$ is $NR^5R^6$ or $CH_2NR^5R^6$ where $R^5$ and $R^6$ are independently hydrogen, $CH_2CO_2H$, $CHPh_2$ or $C(=S)CH_2CH_2CO_2H$, or $R^1$ is $CH_2NR^7CH_2CO_2H$ where $R^7$ is hydrogen, $C_{1-6}$ alkyl or $CO_2CH_2Ph$, or $R^1$ is $C_{1-8}alkyl$ optionally interrupted by one or more oxygen, nitrogen or sulphur atoms and optionally substituted by $CO_2H$, or $R^1$ is $R^8$-$PO(OH)_2$, or -$R^8$tetrazol-5-yl where $R^8$ is a bond, $OCH_2$, $SCH_2$, $CONH$, $CONHCH_2$, $CONHCH_2CONH$, $NHCH_2CONH$ $NHCH(R^3)$, $NR^9(CH_2)q$ where $R^9$ is hydrogen or $C_{1-6}alkyl$ and q is 1 or 2 or $R^{20}$—$CO_2H$ where $R^{20}$ is a bond, $CONHCH_2$ or $NHCH(R^3)$ where $R^3$ is as defined above or $R^1$ is a group of formula (i):

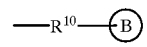

(i)

where B is a 4-, 5-, or 6 membered saturated ring containing a nitrogen atom optionally substituted by hydroxy and substituted by $CO_2H$ or $CONH$-Het where Het is tetrazol-5-yl, or a thiazole or thiadiazole ring substituted by $CO_2H$ or $CH_2CO_2H$, or B is phenyl or a 5-membered aromatic heterocyclic ring containing 1 to 3 heteroatoms selected from nitrogen, oxygen or sulphur optionally substituted by one or more groups selected from $CF_3$, or $CO_2H$, $CH_2OH$, $C_{1-6}alkyl$ optionally interrupted by one or more oxygen atoms, $CH_2CH_2CO_2H$, $C(CO_2H)=N$—OMe, tetrazol-5-yl or $CH_2$tetrazol-5-yl; and $R^{10}$ is a bond, sulphur atom, —CONH—, $CH_2CH_2O$, a group —$NR^{11}$—$CH(CO_2H)$—$CH_2$—, or a group $CONR^{11}(CH_2)_pCONR^{12}$— or —$NR^{11}$—$(CH_2)_p$—$CONR^{12}$— where $R^{11}$ and $R^{12}$ are independently hydrogen or $C_{1-6}alkyl$ and p is a 1 or 2;

$R^2$ is a group of formula (ii) or (iii):

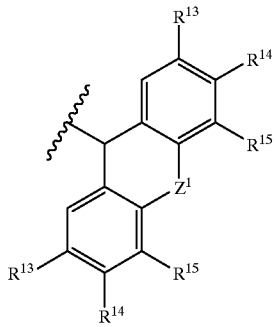

(ii)

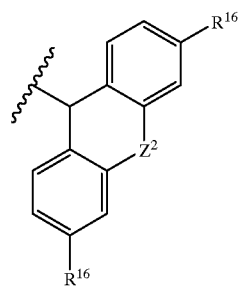
(iii)

where $R^{13}$ groups are independently hydrogen, halogen, methoxy, methylthio or $C_{1-2}$alkyl (optionally substituted by one or more fluorine atoms);

$R^{14}$ groups are independently hydrogen, halogen, hydroxy, $C_{1-3}$alkylthio, $C_{1-4}$alkyl (optionally substituted by one or more fluorine atoms), $C_{3-4}$cycloalkyl, $MeOCH_2$, $MeSCH_2$ or $C_{1-2}$alkoxy;

$R^{15}$ groups are independently hydrogen, halogen or methyl (optionally substituted by one or more fluorine atoms);

$Z^1$ CH=CH, CF=CH or CF=CF;

$Z^2$ is a single bond, oxygen, sulphur, $CH_2CH=CH$, $CH_2CH=CHCH_2$ or $C_{1-4}$alkylene group optionally interrupted by an oxygen or sulphur atom;

$R^{16}$ are independently hydrogen, halogen, $C_{1-2}$alkyl, $CF_3$ or a methylthio group or hydroxy;

$Q^1$ and $Q^2$ each independently represent an O or S;

or a salt thereof, provided that when $Q^1$ is oxygen, $R^2$ is a group of formula (ii).

Alkyl groups, whether alone or as part of another group, can be straight chain or branched. Unless stated otherwise, the term alkyl as used herein refers to $C_{1-6}$alkyl groups, such as methyl, ethyl, propyl and butyl groups.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by sterospecific or asymmetric synthesis. The invention also extends to any tautomeric forms and mixtures thereof.

Suitably X is a bond, $CH_2$ or a $C_{1-3}$alkylene group optionally interrupted by oxygen.

Preferably X is $CH_2$, a bond or $CH_2CH_2O$, more preferably X is $CH_2$.

Suitably R is hydrogen, $NO_2$, $NH_2$, $N(C_{1-6}alkyl)_2$, $CO_2H$, $CH_2OH$, halogen, $CO_2C_{1-6}$alkyl, $C_{1-8}$alkyl optionally interrupted by one or more oxygen, nitrogen or sulphur atoms and optionally substituted by $CO_2H$, or R is hydroxy, phenyl optionally substituted by $CH_2CO_2H$, or $CONR^3R^4$ where $R^3$ and $R^4$ are independently hydrogen, $C_{1-6}$alkyl optionally substituted by hydroxy or $CO_2H$ and/or optionally interrupted by oxygen, nitrogen or sulphur. Preferably R is meta or para relative to the X group. Preferred R groups includes hydrogen, $C_{1-6}$alkoxy, $C_{1-8}$alkyl optionally interrupted by one or two oxygen atoms and optionally substituted by $CO_2H$, $CH_2OH$, hydroxy and halogen. More preferably R is hydrogen, methoxy, $CH_2OCH_2CH_2OCH_3$, $CH_2OCH_2CH_3$, $CH_2OH$, $CH_3$, hydroxy, $OCH_2CO_2H$ or $O(CH_2)_3CO_2H$.

Suitably $R^1$ is $NR^5R^6$ or $CH_2NR^5R^6$ where $R^5$ and $R^6$ are independently hydrogen, $CH_2CO_2H$, $CHPh_2$ or $C(=S)$ $CH_2CH_2CO_2H$, or $R^1$ is $CH_2NR^7CH_2CO_2H$ where $R^7$ is hydrogen, $C_{1-6}$alkyl or $CO_2CH_2Ph$, or $R^1$ is $C_{1-8}$alkyl optionally interrupted by one ore more oxygen, nitrogen or sulphur atoms and optionally substituted by $CO_2H$, or $R^1$ is $-R^8-PO(OH)_2$, or $-R^8$-tetrazol-5-yl where $R^8$ is a bond, $OCH_2$, $SCH_2$, $CONH$, $CONHCH_2$, $CONHCH_2CONH$, $NHCH_2CONH$, $NHCH(R^3)$ or $-R^8-CO_2H$ where $R^8$ is a bond, $CONHCH_2$ $NHCH(R^3)$ where $R^3$ is as defined above or $R^8$ is $NR^9(CH_2)_q$ where $R^9$ is hydrogen or $C_{1-6}$alkyl and q is 1 or 2, or $R^1$ is a group of formula (i) as defined above.

When X is $CH_2$, $R^1$ is preferably meta or para with respect to the X linkage. Preferably $R^1$ is $CO_2H$, $-PO(OH)_2$, $C_{1-8}$alkyl optionally interrupted by one or two oxygen atoms and optionally substituted by $CO_2H$, or $R^1$ is a group of formula (i) where B is phenyl, thiazole, pyrazole optionally substituted by $CO_2H$ or $C_{1-6}$alkyl optionally interrupted by one or two oxygen atoms, or $R^1$ is $NR^5R^6$ or $CH_2NR^5R^6$ where $R^5$ and $R^6$ are independently, $CH_2CO_2H$, $CHPh_2$ or $C(=S)CH_2CH_2CO_2H$, or $R^1$ is $CH_2NR^7CH_2CO_2H$ where $R^7$ is $CO_2CH_2Ph$.

Suitably $R^2$ is a group of formula (ii) or (iii) as defined above. Preferably $R^2$ is a group of formula (ii) where $Z^1$ is CH=CH. Preferably $R^{13}$, $R^{14}$ and $R^{15}$ are all hydrogen.

Suitably $Q^1$ and $Q^2$ each independently represent an O or S. Preferably $Q^1$ is S and $Q^2$ is O or S.

Particularly preferred compounds of the invention include:

3-[[5-[9H-Fluoren-9-yl]-3,4-dihydro-2-oxo-2-4-thioxo-1 (2H)-pyrimidinyl]methyl]benzoic acid, 3-[[5-{5H-Dibenzo[a,d]cyclohepten-5-yl}-3,4-dihydro-2-oxo-4-thioxo-1(2H)-pyrimidinyl]methyl]benzoic acid, 3-[[5-{5H-Dibenzo[a,d]cyclohepten-5-yl}-3,4-dihydro-2-oxo-4-thioxo-1(2H)-pyrimidinyl]methyl] benzeneacetic acid, 3-[[5-{5H-Dibenzo[a,d]cyclohepten-5-yl}-3,4-dihydro-2,4-dioxo-1(2H)-pyrimidinyl]methyl] benzenephosphonic acid, 5-[[5-{5H-Dibenzo[a,d]cyclohepten-5-yl}-3,4-dihydro-2oxo-4thioxo-1-(2H)-pyrimidinyl]methyl]-2-methoxybenzoic acid, 2-[3-[[5-{5-H-Dibenzo[a,d]cyclohepten-5-yl}-3,4-dihydro-2-oxo-4-thioxo-1(2H)-pyrimidinyl]methyl] phenyl]-4-thiazolecarboxylic acid, 3-[[5-{5-H-Dibenzo[a,d]cyclohepten-5-yl}-3,4-dihydro-2-oxo-4-thioxo-1(2H)-pyrimidinyl]methyl]-5-[2-methoxyethoxymethyl]benzoic acid, 3-[[5-{5-H-Dibenzo[a,d]cyclohepten-5-yl}-3,4-dihydro-2-oxo-4-thioxo-1(2H)-pyrimidinyl]methyl]-5-[phenoxymethyl]benzoic acid, 3-[[5-{5-H-Dibenzo[a,d]cyclohepten-5-yl}-3,4-dihydro-2-oxo-4-thioxo-1(2H)-pyrimidinyl]methyl]-5 [ethoxymethyl]benzoic acid, 1-[[3-[[3-Carboxy-5-{5H-dibenzo[a,d]cyclohepten-5-yl}-3,4-dihydro-2-oxo-4-thioxo-1(2H)-pyrimidinyl] methyl]phenyl]methyl]-4-pyrazolecarboxylic acid, 3-[[3-[[3-Carboxy-5-{5H-Dibenzo[a,d]cyclohepten-5-yl}-3,4-dihydro-2-oxo-4-thioxo-1(2H)-pyrimidinyl] methyl]phenyl]methoxy]-5-ethoxybenzoic acid, 3-[[3-Carboxy-5[[5-{5H-dibenzo[a,d]cyclohepten-5-yl}-3,4-dihydro-2-oxo-4-thioxo-1(2H)-pyrimidinyl] methyl]phenyl]methoxy]-5-[2-methoxyethoxy]benzoic acid, 3-[[5-{5H-Dibenzo[a,d]cyclohepten-5-yl}-3,4-dihydro-2-oxo-4-thioxo-1(2H)-pyrimidinyl]methyl]-5-[hydroxymethyl]benzoic acid, 3-[[5-{5H-Dibenzo[a,d]cyclohepten-5-yl}-3,4-dihydro-2-oxo-4-thioxo-1(2H)-pyrimidinyl]methylbenzoic acid, 5-[[5-{5H-Dibenzo[a,d]cyclohepten-5-yl}-3,4-dihydro-2-oxo-4-thioxo-1(2H)-pyrimidinyl]methyl]-2-hydroxybenoic acid, 3-[[5-{5H-Dibenzo[a,d]cyclohepten-5-yl}-3,4-dihydro-2-oxo-4-thioxo-1(2H)-pyrimidinyl]methyl]phenoxy]acetic acid, 2-Bromo-5-[[5-{5H-dibenzo[a,d]cyclohepten-5-yl}-3,4-dihydro-2oxo-4thioxo-1-(2H)-pyrimidinyl]methyl]-benzoic acid, 5-[[-5-{5H-Dibenzo[a,d]cyclohepten-5-yl}-3,4-dihydro-2-oxo-4-thioxo-1(2H)-pyrimidinyl]methyl]-2-[phenylmethyl]benzoic acid, 2-Butyl-5-[[5-{5-H-dibenzo[a,d]cyclohepten-5-yl}-3,4-dihydro-2-oxo-4-thioxo-1(2H)-pyrimidinyl]methyl] benzoic acid, 4-[5-{5-H-Dibenzo[a,d]cyclohepten-5-yl}-3,4-dihydro-2-oxo-4-thioxo-1(2H)-pyrimidinyl]benzoic acid, 5-[[5-{5-H-Dibenzo[a,d]cyclohepten-5-yl}-3,4-dihydro-2-oxo-4-thioxo-1(2H)-pyrimidinyl]methyl]phenyl-1,3-bis[oxyacetic acid], 4-[3-[Carboxymethoxy]-5-[[5-{5H-dibenzo[a,d]cyclohepten-5-yl}-3,4-dihydro-2-oxo-4-thioxo-1(2H)-pyrimidinyl]methyl]phenyl]oxybutanoic acid, 3-[[3-[[5-{5H-Dibenzo[a,d]cyclohepten-5-yl}-3,4-dihydro-2-oxo-4-thioxo-1(2H)-pyrimidinyl]methyl]phenyl][carboxymethyl]amino]-3-thioxobutanoic acid, N-[[3-[[5-{5-Dibenzo-[a,d]cyclohepten-5-yl}-3,4-dihydro-2-oxo-4-thioxo-1(2H)-pyrimidinyl]methyl]phenyl]methyl]-N-[phenylmethoxycarbonyl]glycine, 3-[[5-{5H-Dibenzo[a,d]cyclohepten-5-yl}-3,4-dihydro-2-oxo-4-thioxo-1(2H)-pyrimidinyl]methyl]-5-[[carboxymethyl][diphenylmethyl]amino]benzoic acid, 3-[[5-{5H-Dibenzo[a,d]cyclohepten-5-yl}-3,4-dihydro-2-oxo-4-thioxo-1(2H)-pyrimidinyl]methyl]-5-[carboxymethylamino]benzoic acid, 2-[2-[5-{5H-Dibenzo[a,d]cyclohepten-5-yl}-3,4-dihydro-2-oxo-4-thioxo-1(2H)-pyrimidinyl]ethoxy]benzoic acid, 2-[Carboxymethoxy]-6-[2-[50{5H-dibenzo[a,d]cyclohepten-5-yl}-3,4-dihydro-2-oxo-4-thioxo-1(2H)-pyrimidinyl]ethoxy]benzoic acid, 4-[2-[5-{5H-Dibenzo[a,d]cyclohepten-5-yl}-3,4-dihydro-2-oxo-4-thioxo-1(2H)-pyrimidinyl]ethoxy]-1,3-benzenedioic acid, 3-[[5-{5H-Dibenzo[a,d]cyclohepten-5-yl}-3,4-dihydro-2,4-dithioxo-1(2H)-pyrimidinyl]methyl]benzoic acid, 3-[[5-{5H-Dibenzo[a,d]cyclohepton-5-yl}-3,4-dihydro-4-oxo-2-thioxo-1(2H)-pyrimidinyl]methyl]benzoic acid, and pharmaceutically acceptable salts thereof.

In a further aspect the invention provides a process for the preparation of a compound of formula (I) which comprises reacting a compound of formula (II):

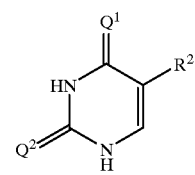

(II)

where $Q^1$, $Q^2$ and $R^2$ are as defined in formula (I) or are protected derivatives thereof with a compound of formula (III):

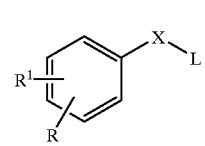

(III)

where R, $R^1$ and X are as defined in formula (I) or are protected derivatives thereof and L is a leaving group, and optionally thereafter in any order:
　removing any protecting groups
　　converting the compound of formula (I) into a further compound of formula (I)
　forming a salt Reaction of compounds of formulae (II) and (III) can be carried out in the presence of a suitable base, for example a metal carbonate such as potassium carbonate or cesium carbonate in a suitable polar solvent such as dimethylformamide or dimethylsulphoxide at 10° C. to 80° C. Preferably L is halogen, in particular bromo. Alternatively the compound of formula (II) can be silylated with a suitable silating reagent such as a trialkylsilychloride and/or 1,1,1,3,3,3-hexamethyldisilazane in a suitable solvent such as pyridine, toluene or 1,4-dioxane at a temperature of about 80° C. to about 140° C. followed by addition of the compound of formula (III) in a suitable solvent such as acetonitrile at elevated temperature, for example at reflux. We prefer to silylate using bis(trimethylsilyl)trifluoroacetamide in refluxing 1,2-dichloroethane followed by treatment with the appropriate compound of formula (III) (where L is halogen, preferably bromide or chloride) in acetonitrile and 1,2-dichloroethane at reflux.

It will be appreciated by those skilled in the art that in the process described above the functional groups of intermediate compounds may need to be protected by protecting groups.

Functional groups of which it is desirable to protect include hydroxy, amino and carboxylic acid. Suitable protecting groups for hydroxy include organosilyl groups (e.g. tert-butyldimethylsilyl, tert-butyldiphenylsilyl or trimethylsilyl), benzyl and tetrahydro-pyranyl. Suitable protecting groups for amino include tert-butoxycarbonyl or benzyloxy carbonyl. Suitable protecting groups for carboxylic acid include $C_{1-6}$alkyl or benzyl esters. The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

In particular compounds of formula (III) where R and $R^1$ contains a carboxylic acid group can be protected as esters, particularly as $C_{1-6}$alkyl esters. Basic hydrolysis of such esters can be performed using metal hydroxides or quaternary ammonium hydroxides such as sodium hydroxide in a solvent such as an aqueous alcohol, 1,4-dioxane, tetrahydrofuran or dimethylformamide at a temperature between 10° C. and 100° C. Where $Q^1/Q^2$ are oxygen, acidic hydrolysis may also be performed using mineral acid such as HCl or a strong organic acid such as trifluoroacetic acid in a suitable solvent such as 1,4-dioxane. We prefer basic hydrolysis using lithium hydroxide in aqueous methanol at ambient temperature.

Compounds of formula (I) where R or $R^1$ is a carboxylic acid can be reacted with an appropriate amine and converted to further compounds of formula (I) using standard methods employed in peptide synthesis, for example using a coupling agent. Coupling agents which may be used include 1,1'-carbonyldiimidazole and 1,3-dicyclohexylcarbodiimide in a suitable solvent such as dimethylformamide, dichloromethane, tetrahydrofuran or acetonitrile at about 0° C. to about 30° C. We prefer to use bromo-tris(pyrrolidino)-phosphonium hexafluorophosphate with a trialkylamine such as N,N-diisopropylethylamine and 4-dimethylaminopyridine in dimethylformamide at ambient temperature.

Compounds of formula (I) where $Q^1$ is oxygen can be converted to a corresponding compound of formula (I) where $Q^1$ is sulphur using standard thiation conditions for conversion of uridine and thymidine nucleosides into their corresponding thio-nucleoside derivatives (see "Chemistry of Nucleosides and Nucleotides" edited by Leroy B. Townsend, Plenum Press volume 1). Thiation may be achieved using reagents such as diphosphorus pentasulphide or Lawesson's reagent in a solvent such as pyridine, 1,4-dioxane, toluene, xylene, or tetrahydrofuran at a temperature of about 50° C. to about 130° C. We prefer to use Lawesson's reagent in 1,4-dioxane at about 100° C.

Compounds of formula (I) where $Q^2$ is S can be prepared from compounds where $Q^2$ is O and $Q^1$ is S. The 4-thioxo group can be alkylated by treatment with a metal bicarbonate or carbonate and an alkyl halide in an appropriate solvent such as an aqueous alcohol at a temperature of 10° C. to 70° C. We prefer to use sodium bicarbonate and methyl iodide in aqueous methanol at 40° C. The 2-position of the uracil can be thiated using the conditions described above, preferably using Lawesson's reagent at 100° C. Treatment of this product with $H_2S$ in a trialkylamine, preferably triethylamine, in pyridine at ambient temperature gives the target compound where $Q^1$ is S and $Q^2$ is S. Alternatively the 4-alkylthio compound can be hydrolysed to compounds of formula (I) where $Q^2$ is S and $Q^1$ is O by treatment with HCl in aqueous alcohol at a temperature of 60–100° C. preferably with 2M HCl in aqueous ethanol at reflux.

Compounds of formula (II) where $Q^1$ and $Q^2$ are oxygen can be prepared by reaction of a compound of formula (IV):

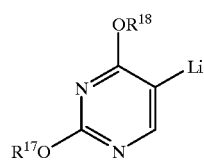

(IV)

where $R^{17}$ and $R^{18}$ are independently $C_{1-6}$alkyl or benzyl with a compound of formula (V) or (VI):

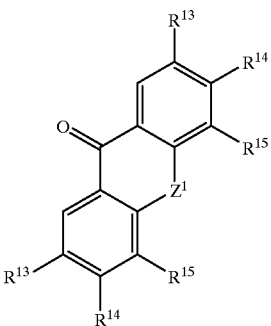

(V)

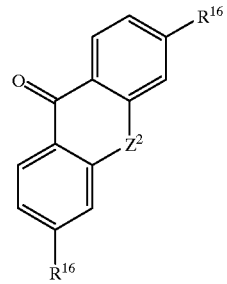

(VI)

where $Z^1$, $Z^2$, $R^{13}$, $R^{14}$, $R^{15}$ and $R^{16}$ are as defined in formula (I) followed by reduction of the resulting alcohol. Compounds of formula (IV) are prepared by treating the corresponding halide with an alkyl lithium reagent (alkyl=n-Butyl, sec-Butyl, tert-Butyl) in solvents such as tetrahydrofuran or diethyl ether at low temperature e.g. −40° C. to −78° C.

The resulting alcohol can then be reduced and deprotected to compounds of formula (II) by treatment with a trialkylsilane such as triethylsilane in a suitable solvent such as dichloromethane, chlorform, or 1,2-dichloroethane and an acid or Lewis acid such as trifluoroacetic acid or borontrifluoride diethyl ether complex. We preferred to perform the metal halogen exchange on 5-bromo-2,4-bis(1,1-dimethylethoxy)pyrimidine using n-butyllithium at about −78° C. in tetrahydrofuran.

When the lithio species is quenched with a substituted 10,11-dihydro-5H-dibenzo[a,d]cyclohepten-5-one the resulting substituted 10,11-dihydro-5-(2,4-bis(alkoxy)pyrimidin-5-yl)-5H-dibenzo[a,d]cyclohepten-5-ol can then be converted to the uracil (II) (where $Z^1$ is CH=CH) by refluxing in a carboxylic acid solvent (Chem. Ber., 1989, 122, 1595). We prefer to use acetic acid. In some cases further treatment with trifluoroacetic acid at reflux may be required for the dehydration to give the substituted uracil (II).

Compounds of formula (II) can also be prepared from uracil and the appropriately substituted 5H-dibenzo[a,d] cyclohepten-5-ol by refluxing in a carboxylic acid solvent such as acetic acid (J. Org. Chem., 1974, 39, 587).

Compounds of formula (III) where X is $CH_2$ can be prepared from compounds of formula (VII):

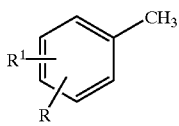

(VII)

where R and R¹ are as defined in formula (I) by treating with, for example, a halogenating agent. Suitable reagents include N-bromosuccinimide in a suitable solvent such as chloroform, dichloromethane, ethyl acetate or benzene at elevated temperature and irradiated with strong light. Preferably the reaction is carried out in the presence of a catalytic amount of benzoyl peroxide at reflux and irradiated with a 500W halogen lamp.

Compounds of formula (I) in which X is a bond can be prepared by reacting compounds of formula (II) with compounds of formula (VIII):

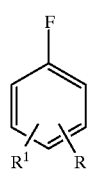

(VIII)

where R and R¹ are as defined in formula (I). The reaction can be carried out in the presence of a suitable base, for example a metal carbonate such as cesium carbonate in a suitable polar solvent such as dimethylformamide or dimethylsulphoxide at about 50–130° C. Preferably the reaction is carried out using cesium carbonate in dimethylformamide at about 100° C.

Salts of the compounds of formula (I) may be formed by reacting the free acid, or a salt thereof, with one or more equivalents of the appropriate base (for example ammonium hydroxide optionally substituted by $C_{1-6}$alkyl or an alkali metal or alkaline earth metal hydroxide). The reaction may be carried out in a solvent or medium in which the salt is insoluble or in a solvent in which the salt is soluble, e.g. water, alcohol or acetone, which may be removed in vacuo, or by freeze drying. The reaction may also be a metathetical process or it may preferably be carried out on an ion exchange resin. The non-toxic pharmaceutically acceptable salts are preferred although other salts may be useful, e.g. in isolating or purifying the product.

Novel intermediate form a further aspect of the invention.

The compound of the invention have been submitted to the assay outlined below and have been found to be P2 7-TM G-protein receptor antagonists, particularly to the P2Y2 receptor. Accordingly they are useful in therapy and are, in particular, indicated for use as anti-inflammatory agents useful in a number of inflammatory diseases such as asthma, inflammatory bowel disease, ARDS, psoriasis, rheumatoid arthritis, myocardial ischaemia, COPD, cystic fibrosis, arthereosclerosis, restenosis, peridontal disease, septic shock, osteoarthritis and stroke. The compounds of the invention can be co-administered with other anti-inflammatory agents. ATP receptors have also been reported on tumour cells and may be involved in the development of cancer. Antagonists may therefore be useful in treatment of cancer.

The invention provides in a further aspect a method of treating an inflammatory condition which comprise administering to a patient in need of therapy, a therapeutically effective amount of a compound of the invention.

According to the invention there is further provided use of the compounds of the invention in the manufacture of a medicament for use in the treatment of an inflammatory condition.

The compounds may be administered orally, topically e.g. to the lung and/or the airways, in the form of solutions, suspensions, HFA areosols and dry powder formulations, e.g. Turbuhaler® formulations or by parenteral administration in the form of sterile parenteral solutions or suspensions.

The invention further provides a pharmaceutical composition comprising a compound according to the present invention in association with a pharmaceutically acceptable excipient an/or adjuvant. Particularly preferred are compositions not containing material capable of causing an adverse, e.g. an allergic, reaction. For example a chelating or sequestering agent, an antioxidant, a tonicity adjusting agent, a pH modifying agent and/or a buffering agent are suitable additives.

The compound of the invention may also be administered by means of a dry powder inhaler. The inhaler may be a single or a multi dose inhaler, and may be a breath actuated dry powder inhaler.

A pharmaceutical composition according to the present invention could optionally be prepared in freeze dried from using any lyophilisation techniques commonly used within the pharmaceutical area. Upon use but before administration, such pharmaceutical compositions are generally reconstituted in a pharmaceutically acceptable excipient. Preferably a solution of the pharmaceutical composition according to the invention obtained after reconstitution is an isotonic solution. Such a pharmaceutical composition according to the present invention when reconstituted is preferably administered by injection, for example intravenously, subcutaneously or intramuscularly.

The invention is illustrated by the following examples which should not be interpreted as limiting the invention. In the examples the NMR spectra were measured on a Varian Unity Inova 300 or 400 MHz spectrometer and the MS spectra measured as follows: EI spectra were obtained on a VG 70-250S or Finnigan Mat Incos-XL spectrometer, ESI and APCI spectra were obtained on Finnigan Mat SSQ7000 or a Micromass Platform spectrometer. Where necessary, the reactions were performed under an inert atmosphere of either nitrogen or argon. Where necessary, preparative HPLC separations were generally performed using a Novapak®, Bondapak®, or Hypersil® column packed with BDSC-18 reverse phase silica gel. Chromatography was generally performed using Matrex Silica 60® (35–70 micron)or Prolabo Silica gel 60® (35–75 micron) suitable for flash silica gel chromatography.

Example 1

3-[[5-[9H-Fluoren-9-yl]-3,4-dihydro-2-oxo-4-thioxo-1(2H)-pyrimidinyl]methyl]benzoic acid i) 5-[9-Hydroxy-9H-fluoren-9-yl]-2', 3', 5', -tris-O-[[1,1-dimethylethyl]dimethylsily]uridine To a solution of 2', 3', 5', -tris-O-[[1,1-dimethylethyl]dimethylsily]uridine (Synthesis, 1991, 4, 283) (25 g) and N,N,N',N'-tetramethylethylenediamine (12.5 ml) in tetrahydrofuran (300 ml) at −78° C. was added sec-butyllithium (82 ml of a 1.3 M solution in cyclohexane) over 10 minutes. After 45 minutes, a solution of 9-fluorenone (13 g) in tetrahydrofuran (40 ml) was added. The mixture was allowed to warm to room temperature and stirred overnight. The reaction was treated with saturated aqueous ammonium chloride and extracted with dichloromethane. The combined extracts were dried (MgSO$_4$) and evaporated. Purification was by chromatography eluting with 50% acetone in isohexane.

Yield 19.77 g.

MS: FAB(−ve): 765 (M−1)

ii) 5-[9H-Fluoren-9-yl]uridine

To a solution of the product of step (i) (10 g) and triethylsilane (2.3 ml) in dichloromethane (50 ml) at 0° C. was added boron trifluoride diethyl etherate (3.2 ml). The mixture was stirred for 45 minutes then evaporated to dryness and azeotroped with toluene. The residue was dissolved in tetrahydrofuran (25 ml), treated with tetrabutyl ammonium fluoride (16.8 g) and the mixture stirred overnight. The mixture was evaporated and the residue purified by chromatography eluting with 10% methanol in dichloromethane. Yield 5 g.

MS:FAB(+ve): 409 (M+1)

iii) 5-[9H-Fluoren-9-yl]-3,4-dihydro-2,4(1H, 3H)-pyrimidinedione

A mixture of the product from step (ii) (0.67 g), ethanol (5 ml) and 6M HCl (20 ml) was heated at reflux for 84 hours. The mixture was concentrated under reduced pressure and water added. The resultant precipitate was filtered off and dried. Yield 0.34 g.

1H NMR: δ (DMSO) 11.20(br s, 1H), 10.71(br s, 1H), 7.90(d,2H), 7.50-7.20(d+t+t,6H), 6.90(br s,1H), 5.00(s,1H).

iv) 3-[[5-[9H-Fluoren-9-yl]-3,4-dihydro-2,4-dioxo-1 (2H)-pyrimidinyl]methyl]benzoic acid, methyl ester To a stirred solution of the product from step (iii) (0.5 g) in dimethylformamide (5 ml) at room temperature was added tetraethylammonium hydroxide (1.31 ml). After 10 minutes methyl 3-bromomethylbenzoate (0.435 g) was added and the mixture was stirred for 20 minutes. The mixture was partitioned between ethyl acetate and water. The organic phase was dried (MgSO$_4$) and evaporated. Purified by chromatography eluting with 20–40% ethyl acetate in isohexane. Yield 0.23 g.

MS: EI(+ve): 424 (M$^+$)

v) 3-[[5-[9H-Fluoren-9-yl]-3,4-dihydro-2-oxo-4-thioxo-1 (2H)-pyrimidinyl]methyl]benzoic acid, methyl ester A mixture of the product from step (iv) (0.3 g) and Lawesson's reagent (0.286 g) in tetrahydrofuran (8 ml) was heated at reflux for 6 hours then cooled and partitioned between ethyl acetate and aqueous sodium bicarbonate. The organic phase was dried (MgSO$_4$) and evaporated. Purified by chromatography eluting with 30–40% ethyl acetate in isohexane.

Yield 0.19 g

MS:FAB(+ve): 441 (M+1)

vi) 3-[[5-[9H-Fluoren-9-yl]-3,4-dihydro-2-oxo-4-thioxo-1(2H)-pyrimidinyl]methyl]benzoic acid A mixture of the product from step (v) (0.175 g) and lithium hydroxide monohydrate (0.034 g) in tetrahydrofuran (3 ml) and water (3 ml) was stirred at room temperature for 3 hours and partitioned between dichloromethane and 2 M HCl. The organic phase was dried (MgSO$_4$) and evaporated under reduced pressure. Yield 0.095 g.

MS:FAB(+ve): 427 (M+1, 100%)

1H NMR: δ (DMSO) 13.16(s,1H), 13.05(br s, 1H), 8.00-7.22(m, 12H), 7.04(s,1H), 5.99(s,1H), 4.84(s, 2H) plus rotamer.

MP: 261–263° C.

Example 2

3-[[5-[5H-Dibenzo[a,d]cyclohepten-5-yl]-3,4-dihydro-2-oxo-4-thioxo-1(2H)-pyrimidinyl]methyl] benzoic acid i) 5-Bromo-2,4-bis(1,1-dimethylethoxy)pyrimidine To a solution of potassium tert-butoxide (67.5 g) in tetrahydrofuran (500 ml) was added dropwise a solution of 5-bromo-2,4-dichloropyrimidine (55 g) (J.Am.Chem.Soc. 1934, 56, 134) in tetrahydrofuran (100 ml). After 1.5 hours, water (100 ml) was added carefully and the mixture extracted with ethyl acetate. The combined extract was washed with water, dried (MgSO$_4$) and evaporated under reduced pressure. Purification was by chromtography eluting with isohexane. Yield 52.4 g.

MS: GC-MS: 302/304 (M$^+$)

ii) 5-(5H-Dibenzo[a,d]cyclohepten-5-yl)-2,4(1H,3H)-pyrimidinedione

To a solution of the product of step (i) (50 g) in dry tetrahydrofuran (1l) at −78° C. was added n-butyllithium (69 ml of a 2.5 M solution in hexanes) dropwise. After 0.5 hours a solution of 5H-dibenzo[a,d]cyclohepten-5-one (44 g) in tetrahydrofuran (100 ml) was added. The reaction mixture was stirred at −78° C. for three hours and then allowed to warm to room temperature overnight. Saturated aqueous ammonium chloride solution (400 ml) was added and the mixture extracted with ethyl acetate. The organic solution was dried (MgSO$_4$) and evaporated under reduced pressure to give the crude 5-[2,4-bis[1,1-dimethylethoxy] pyrimidin-5-yl]-5H-dibenzo[a,d]cyclohepten-5-ol which was used directly.

To stirred solution of this product and triethylsilane (64 ml) in dry dichloromethane (400 ml) at 0° C. was added trifluoroacetic acid (150 ml) dropwise over ten minutes. The cooling bath was removed and the solution was stirred at room temperature overnight. Toluene (300 ml) was added and solution was evaporated under vacuum. The residue was azeotroped with toluene (3 times). The oil was treated with diethyl ether and the precipitated product collected as a white powder. Yield 44 g.

MS: EI: 302 (M+, 100%)

iii) 3-[[5-{5H-Dibenzo[a,d]cyclohepten-5-yl}-3,4-dihydro-2,4-dioxo-1(2H)-pyrimidinyl]methyl]benzoic acid, methyl ester To a solution of the product from step (ii) (0.7 g) in DMSO (5 ml) was added cesium carbonate (0.75 g). After 5 minutes a solution of 3-bromomethylbenzoic acid methyl ester (0.53 g) in DMSO (5 ml) was added. The mixture was stirred at room temperature for 20 minutes and partitioned between ethyl acetate and water. The organic phase was washed with water and brine, dried (MgSO$_4$) and evaporated. Purified by chromatography eluting with 30% ethyl acetate in isohexane. Yield 0.34 g.

MS: FAB(+ve): 451 (M+1)

iv) 3-[[5-{5H-Dibenzo[a,d]cyclohepten-5-yl}-3,4-dihydro-2-oxo-4-thioxo-1(2H)-pyrimidinyl]methyl]benzoic acid, methyl ester The subtitle compound was prepared from the product of step (iii) (0.34 g) by the method of example 1 step (v). Yield 0.22 g.

MS: FAB(+ve): 467 (M+1)

v) 3-[[5-{5H-Dibenzo[a,d]cyclohepten-5-yl}-3,4-dihydro-2-oxo-4-thioxo-1(2H)-pyrimidinyl]methyl]benzoic acid The title compound was prepared from the product of step (iv) (0.22 g) by the method of example 1 step (vi). Yield 0.04 g.

MS: FAB(+ve): 453 (M+1)

1H NMR: δ (DMSO) 13.16(br s,1H), 12.65(s,1H), 7.96 (d,1H), 7.85(s,1H), 7.60-7.50(m,4H), 7.36-7.23(m,6H), 6.99 (s,1H), 6.73(s,2H), 5.80(s,1H), 4.89(s,2H).

MP:>230° C.

Example 3

3-[[5-{5H-Dibenzo[a,d]cyclohepten-5-yl}-3,4-dihydro-2-oxo-4thioxo-1(2H)- pyrimidinyl]methyl] benzeneacetic acid i) 3-[Bromomethyl]benzeneacetic acid, ethyl ester A mixture of [3-methylphenyl]acetic acid ethyl ester (5g), N-bromosuccinimide (5 g) and benzoyl peroxide (0.1 g) in dichloromethane (200 ml) was irradiated under a 500 W halogen lamp for 6 hours. The solvent was evaporated and the residue partitioned between diethyl ether and water. The organic phase was dried (MgSO$_4$) and evaporated. Purified by chromatography eluting with 5–10% ethyl acetate in isohexane. Yield 5.14 g.

MS: GC-MS: 256/258 (M$^+$)

ii) 3[[5-{5H-Dibenzo[a,d]cyclohepten-5-yl}-3,4-dihydro-2,4-dioxo-1(2H)-pyrimidinyl]methyl]benzeneacetic acid, ethyl ester The subtitle compound was prepared from the product of step (i) (0.85 g) and example 2 step (ii) (1.0 g) by the method of example 2 step (iii). Purification was by chromatography eluting with 50% ethyl acetate in isohexane. Yield 0.74 g.

MS: FAB(+ve): 479 (M+1, 100%)

iii) 3-[[5{5-Dibenzo[a,d]cyclohepten-5-yl}-3,4-dihydro-2-oxo-4-thioxo-1(2H)-pyrimidinyl]methyl]benzeneacetic acid, ethyl ester The subtitle compound was prepared from the product of step (ii) (0.6 g) by the method of example 1 step (v). Purification was by chromatography eluting with 20% ethyl acetate in isohexane. Yield 0.37 g.

MS: APCI(+ve): 495 (M+1, 100%)

iv) 3-[[5-{5H-Dibenzo[a,d]cyclohepten-5-yl}-3,4-dihydro-2-oxo-4-thioxo-1(2H)-pyrimidinyl]methyl] benzeneacetic acid The title compound was prepared from the product of step (iii) (0.36 g) by the method of example 1 step (vi). Yield 0.19 g.

MS: APCI(+ve): 467 (M+1, 100%)

1H NMR: δ (DMSO) 12.62(s,1H), 12.45(br s,1H), 7.58-7.08(m, 12H), 6.89(s,1H), 6.62(s,2H), 5.79(s,1H), 4.78(s, 2H), 3.63(s,2H).

MP: 135–137° C.

Example 4

3[[5-{5H-Dibenzo[a,d]cyclohepten-5yl}-3,4-dihydro-2,4-dioxo-1(2H)-pyrimidinyl]methyl] benzenephosphonic acid i) 3-Methylbenzenephosphonic acid, diethyl ester To a solution of 3-bromotoluene (5 g) in tetrahydrofuran at −78° C. was added tert-butyllithium (35 ml of a 1.7 M solution in pentane). The mixture was stirred at −78° C. for 1 hour and diethl chlorophosphate (5.1 ml) was added. After 2 hours the mixture was warmed to 0° C., quenched with aqueous ammonium chloride and partitioned between ethyl acetate and water. The organic phase was dried (MgSO$_4$) and evaporated. Purified by chromatography eluting with 40% ethyl acetate in isohexane. Yield 2.7 g.

MS: GC-MS: 228 (M$^+$)

ii) 3-[Bromomethyl]benzenephosphonic acid, diethyl ester

The subtitle compound was prepared from the product of step (i) (2.64 g) by the method of example 3 step (i). Purification was by chromatography eluting with 40% ethyl acetate in isohexane. Yield 1.42 g.

MS: GC-MS: 306/8 (M$^+$)

iii) 3-[[5-{5H-Dibenzo[a,d]cyclohepten-5-yl}-3,4-dihydro-2,4-dioxo-1(2H)-pyrimidinyl]methyl] benzenephosphonic acid, diethyl ester The subtitle compound was prepared from the product of step (ii) (1.27 g) by the method of example 2 step (iii). Yield 0.5 g.

MS: FAB(+ve): 529 (M+1, 100%)

iv) 3-[[5-{5H-Dibenzo[a,d]cyclohepten-5-yl}-3,4-dihydro-2,4-dioxo-1(2H)-pyrimidinyl]methyl] benzenephosphonic acid, diethyl ester To a stirred solution of the product from step (iii) (0.5 g) in dimethylformamide (10 ml) at 0° C. was added trimethylsilyl bromide (0.265 ml). After 1 hour the mixture was stirred at room temperature and then treated with a further 0.265 ml trimethylsilyl bromide. Two further aliquots were added after 2 and 4 hours. The mixture was evaporated and the residue dissolved in methanol (10 ml) and stirred overnight. The solution was concentrated under reduced pressure to 5 ml and treated with sodium bicarbonate (0.21 g) and water (5 ml). The mixture was stirred for 10 minutes and purified by reverse phase chromatography. The product was obtained by lyophilisation. Yield 0.085 g.

MS: APCI(+ve): 472 (M−2Na+2)

1H NMR: δ (D$_2$O) 7.59-7.15(m,11H), 6.76(d,1H), 6.59(s, 2H), 6.37(s,1H), 5.13(s,1H), 4.37(s,1H).

MP: 348° C.

Example 5

5-[[5-{5H-Dibenzo[a,d]cyclohepten-5-yl}-3,4-dihydro-2-oxo-4-thioxo-1(2H)-pyrimidinyl]methyl]-2-methoxybenzoic acid i) 5-Bromomethyl-2-methoxybenzoic acid, methyl ester A mixture of 2-methoxy-5-methylbenzoic acid methyl ester (J.Chem.Soc.Perkin Trans.1, 1994, 1125) (1.47 g) and N-bromosuccinimide (1.45 g) in benzene (15 ml) was irradiated under a 500 W halogen lamp for 3 hours. The solvent was evaporated and the residue triturated with diethyl ether. The succinimide was filtered off and the filtrate evaporated. The residue was triturated with isohexane and the product collected by filtration. Yield 1.41 g. Used directly in the next step.

ii) 5-[[5-{5H-Dibenzo[a,d]cyclohepten-5-yl}-3,4-dihydro-2,4-dioxo-1(2H)-pyrimidinyl]methyl]-2-methoxybenzoic acid, methyl ester The subtitle compound was prepared from the product of step (i)(0.9 g) and example 2 step (ii) (1.05 g) by the method of example 2 step (iii). Purification was by chromatography eluting with 30% ethyl acetate in isohexane. Yield 0.36 g.

1H NMR: δ (DMSO) 11.20(s,1H), 7.55(d,4H), 7.40–7.25 (m,8H), 7.20(d,1H), 6.70(s,2H), 6.60(s,1H), 5.30(s,1H), 4.70(s,2H), 3.86(s,6H).

iii) 5-[[5-{5H-Dibenzo[a,d]cyclohepten-5-yl}-3,4-dihydro-2-oxo-4-thioxo-1(2H)-pyrimidinyl]methyl]-2-methoxybenzoic acid, methyl ester A mixture of the product from step (ii) (0.36 g) and phosphorous pentasulphide (0.66 g) in dry pyridine (10 ml) was heated at 115° C. for 16 hours. The mixture was partitioned between ethyl acetate and water. The organic phase was washed with brine, dried (MgSO$_4$) and evaporated. Purified by chromatography eluting with 40% ethyl acetate in isohexane. Yield 0.16 g.

MS: FAB(+ve): 497 (M+1)

iv) 5-[[5-{5H-Dibenzo[a,d]cyclohepten-5-yl}-3,4-dihydro-2-oxo-4-thioxo-1(2H)-pyrimidinyl]methyl]-2-methoxybenzoic acid.

The title compound was prepared from the product of step (iii) (0.126 g) by the method of example 1 step 9 vi).

Yield 0.063 g.

MS: APCI(+ve): 483 (M+1, 100%)

1H NMR: δ (DMSO) 12.83(br,s,1H), 12.60(s,1H), 7.57 (m,3H), 7.40-7.20(m,7H), 7.18(d,1H), 6.94(s,1H), 6.73(s, 2H), 5.79(s,1H), 4.76(s,2H), 3.87(s,3H).

Example 6

2-[3-[[5-{5H-Dibenzo[a,d]cyclohepten-5yl}-3,4-dihydro-2oxo-4-thioxo-1(2H)-pyrimidinyl]methyl]phenyl]-4-thiazolecarboxylic acid i) 2-[3-Methylphenyl]-4-thiazolecarboxylic acid, ethyl ester Hydrogen sulphide gas was bubbled into a solution of m-toluonitrile (10 g) in triethylamine (30 ml) and pyridine (20 ml) for 3 hours. The solvents were evaporated and the residue azeotroped with toluene then passed through a plug of silica gel eluting with 10% ethyl acetate in dichloromethane. A mixture of the product (9.05 g) and ethyl bromopyruvate (9 ml) in ethanol (175 ml) was heated at reflux overnight. The mixture was evaporated and the reside partitioned between ethyl acetate and saturated aqueous sodium bicarbonate. The organic phase was dried (MgSO$_4$) and evaporated. Purified by chromatography eluting with 20% ethyl acetate in isohexane. Yield 7.91 g. Used directly in the next step.

ii) 2-[3-[Bromomethyl]phenyl]-4-thiazolecarboxylic acid, ethyl ester

The subtitle compound was prepared from the product from step (i) (3 g) by the method of example 5 step (i). Yield 2.2 g, Used directly in the next step.

iii) 2-[3-[[5-{5H-dibenzo[a,d]cyclohepten-5-yl}-3,4-dihydro-2,4-dioxo-1-(2H)-pyrimidinyl]methyl]-phenyl]-4-thiazolecarboxylic acid, methyl ester The subtitle compound was prepared from the product of step (ii) (0.87 g) by the method of example 2 step (iii). Purification was by chromatography eluting with 30% ethyl acetate in isohexane. Yield 1.0 g. Used directly in the next step.

iv) 2-[3-[[5-{5H-dibenzo[a,d]cyclohepten-5-yl}-3,4-dihydro-2-oxo-4-thioxo-1(2H)-pyrimidinyl]methyl]-phenyl]-4-thiazolecarboxylic acid, ethyl ester The subtitle compound was prepared from the product of step (iii) (1.1 g) by the method of example 1 step (v) using 1,4-dioxane as solvent. Yield 0.5 g.

MS: ESI(+ve): 564 (M+1, 100%)

v) 2-[[3-{5H-Dibenzo[a,d]cyclohepten-5-yl}-3,4-dihydro-2-oxo-4-thioxo-1(2H)-pyrimidinyl]methyl]phenyl]-4-thiazolecarboxylic acid The title compound was prepared from the product of step (iv) (0.3 g) by the method of example 1 step (vi). Yield 0.22 g.

MS: APCI(+ve): 536 (M+1, 100%)

1H NMR: δ (DMSO) 13.26(br,s,1H), 12.64(br,s1H), 8.59 (s,1H), 8.00(d,1H), 7.98(s,1H), 7.60-7.20(m,10H), 7.00(s, 1H), 6.78(s,2H), 5.79(s,1H), 4.91(s,2H).

MP: 165° C.

Example 7

3-[[5-{5H-Dibenzo[a,d]cyclohepten-5yl}-3,4-dihydro-2oxo-4-thioxo-1(2H)-pyrimidinyl]methyl]-5-[2-methoxyethoxymethyl]benzoic acid i) 3-Bromomethyl-5-[2-methoxyethoxymethyl]benzoic acid ethyl ester Sodium hydride (0.357 g, 60% dispersion in oil) was added to 2methoxyethanol (10 ml) with stirring. After 10 minutes 3,5-bis[bromomethyl]benzoic acid ethyl ester (J. Chem. Soc. Chem. Commun. 1992, 22, 1647) (3 g) was added and the mixture stirred for 3 hours. The mixture was partitioned between ethyl acetate and water. The organic phase was dried (MgSO$_4$) and evaporated. Purified by chromatography eluting with 20% ethyl acetate in isohexane. Yield 0.45 g.

MS: GC-MS: 330/2 (M$^+$)

ii) 3-[[5-{5H-dibenzo[a,d]cyclohepten-5-yl}-3,4-dihydro-2,4-dioxo-1(2H)-pyrimidinyl]methyl]-5-[2-methoxyethoxymethyl]benzoic acid, ethyl ester A mixture of example 2 step (ii) (0.41 g) and bis[trimethylsilyl]trifluoroacetamide (0.73 g) in 1,2-dichloroethane (10 ml) was heated at reflux for 1 hour. The product from step (i) (0.45 g) was added and the mixture was heated at reflux for 7 hours. The mixture was evaporated and the residue purified by chromatography eluting with 30% ethyl acetate in isohexane. Yield 0.52 g.

MS: APCI(+ve): 553 (M+1)

iii) 3-[[5-{5H-Dibenzo[a,d]cyclohepten-5-yl}-3,4-dihydro-2-oxo-4-thioxo-1(2H)-pyrimidinyl]methyl]-5-[2-methoxyethoxymethyl]benzoic acid, ethyl ester The subtitle compound was prepared from the product of step (ii) (0.52 g) by the method of example 6 step (iv). Purification was by chromatography eluting with 30–20% ethyl acetate in toluene. Yield 0.457 g.

MS: APCI(+ve): 569 (M+1, 100%)

iv) 3-[[5-{5H-Dibenzo[a,d]cyclohepten-5-yl}-3,4-dihydro-2-oxo-4-thioxo-1(2H)-pyrimidinyl]methyl]-5-[2-methoxyethoxymethyl]benzoic acid The title compound was prepared from the product of step (iii) (0.457 g) by the method of example 1 step (vi). Yield 0.216 g.

MS: APCI(+ve): 541 (M+1, 100%)

1H NMR: δ (DMSO) 12.64(s,1H), 7.92(s,1H), 7.76(s, 1H), 7.58(d,2H), 7.45(s,1H), 7.37-7.23(m,6H), 6.97(s,1H), 6.72(s,2H), 5.80(s,1H), 4.88(s,2H), 4.59(s,2H), 3.67(m,2H), 3.52(m,2H), 3.27(s,3H).

MP: 194–195° C.

Example 8

3-[[5-{5H-Dibenzo[a,d]cyclohepten-5-yl}-3,4-dihydro-2-oxo-4-thioxo-1(2H)-pyrimidinyl]methyl]-5-[phenoxymethyl]benzoic acid i) 3-Bromomethyl-5-[phenoxymethyl]benzoic acid ethyl ester The subtitle compound was prepared from 3,5-bis[bromomethyl]benzoic acid ethyl ester (5.18 g) and phenol (1.45 g) in dimethylformamide (10 ml) by the method of example 7 step (i). Yield after chromatography, eluting with 10% ethyl acetate in isohexane, 2.13 g of a mixture containing 15% product and 85% diphenoxy compound.

MS: GC-MS: 248/9 (15%)

ii) 3-[[5-{5H-Dibenzo[a,d]cyclohepten-5-yl}-3,4-dihydro-2,4-dioxo-1(2H)-pyrimidinyl]methyl]-5-[phenoxymethyl]benzoic acid, ethyl ester The subtitle compound was prepared from the product of step (i) (1.29 mmol) and example 2 step (iv) (0.39 g) by the method of example 7 step (ii). Purification was by chromatography eluting with 30% ethyl acetate in isohexane. Yield 0.564 g.

MS: APCI(+ve): 561 (M+1 %)

iii) 3-[[5-{5H-Dibenzo[a,d]cyclohepten-5-yl}-3,4-dihydro-2-oxo-4-thioxo-1(2H)-pyrimidinyl]methyl]-5-[phenoxymethyl]benzoic acid, ethyl ester The subtitle compound was prepared from the product of step (ii) (0.564g) by the method of example 6 step (iv). Purification was by chromatography eluting with 25% ethyl acetate in toluene. Yield 0.44 g.

MS: APCI(+ve): 587 (M+1, 100%)

iv) 3-[[5-{5H-Dibenzo[a,d]cyclohepten-5-yl}-3,4-dihydro-2-oxo-4-thioxo-1(2H)-pyrimidinyl]methyl]-5-[phenoxymethyl]benzoic acid The title compound was prepared from the product of step (iii) (0.44 g) by the method of example 1 step (vi). Purified by reverse phase HPLC. Yield 0.037 g.

MS: APCI(+ve): 559 (M+1)

1H NMR δ (DMSO) 8.05(s,1H), 7.81(s, 1H), 7.60-7.57 (m,3H), 7.38-7.21(m,8H), 7.08-7.04(m,2H), 7.00-6.95(m, 2H), 6.72(s,2H),5.80(s,1H),5.21(s,2H),4.91(s,2H).

MP: 160–165° C.

Example 9

3-[[5-{5-H-Dibenzo[a,d]cyclohepten-5-yl}-3,5-dihydro-2-oxo-4thioxo-1(2H)-pyrimidinyl]methyl]-5-[ethoxymethyl]benzoic acid i) 3-Bromomethyl-5-{ethoxymethyl}benzoic acid, ethyl ester A stirred solution of 3,5-bis[bromomethyl]benzoic acid ethyl ester (3g) in ethanol (100 ml) was treated with potassium ethoxide (0.75 g) and stirred overnight. The mixture was partitioned between ethyl acetate and water. The organic phase was dried (MgSO$_4$) and evaporated and the residue purified by chromatography eluting with 10% ethyl acetate in isohexane. Yield 1.3 g.

MS: GC-MS: 300/302 (M$^+$)

ii) 3-[[5-{5H-Dibenzo[a,d]cyclohepten-5yl}-3,4-dihydro-2,4-dioxo-1(2H)-pyrimidinyl]methyl]-5-[ethoxymethyl]benzoic acid, ethyl ester The subtitle compound was prepared from the product of step (i) (1.3 g) and example 2 step (ii) (1.31 g) by the method of example 7 step (ii), Yield 1.28 g.

MS:ESI(+ve): 523 (M+1, 100%)

iii) 3-[[5-{5H-Dibenzo[a,d]cyclohepten-5-yl}-3,4dihydro-2-oxo4-thioxo-1(2H)-pyrimidinyl]methyl]-5-[ethoxymethyl]benzoic acid, ethyl ester the subtitle compound was prepared from the product of step (ii) (1.28 g) by the method of example 6 step (iv). Yield 0.86 g.

MS: APCI(+ve): 539 (M+1)

iv) 3-[[5-{5H-Dibenzo[a,d]cyclohepten-5-yl}-3,4-dihydro-2-oxo-4-thioxo-1(2H)-pyrimidinyl]methyl]-5-[ethoxymethyl]benzoic acid The title compound was prepared from the product of step (iii) (0.85 g) by the method of example 1 step (vi). Purified by reverse phase HPLC. Yield 0.113 g.

MS: APCI(+ve); 51 (M+1, 100%)

1H NMR δ (DMSO) 12.64(s,1H), 7.91(s, 1H), 7.76(s, 1H), 7.58(d,2H), 7.44(s,1H), 7.37-7.22(m,6H), 6.98(s,1H), 6.72(s,2H), 5.80(s,1H), 4.88(s,2H), 4.55(s,2H), 3.55(q,2H), 1.20(t,3H).

MP:>240° C.

Example 10

1-[[3-[[3Carboxy-5-{5H-dibenzo[a,d]cyclohepten-5yl}-3,4-dihydro-2-oxo-4-thioxo-1(2H)-pyrimidinyl] methyl]phenyl]methyl]-4pyrazolecarboxylic acid, ethyl ester A solution of ethyl 4-pyrazolecarboxylic (0.5 g) in dimethylformamide (3 ml) was added dropwise to a suspension of sodium hydride (0.143 g) in dimethylformamide (7 ml). The mixture was stirred for 1.5 hours and transferred into a solution of 3,5bis[bromomethyl]benzoic acid ethyl ester in dimethylformamide (30 ml). The mixture was stirred at room temperature for 2 hours and partitioned between ethyl acetate and water. The organic phase was dried (MgSO$_4$), evaporated and purified by chromatography eluting with 20% ethyl acetate in isohexane. Yield 0.8 g.

1H NMR δ (CDCl$_3$) 8.04(s,1H), 7.96(s, 1H), 7.92(s,1H), 7.87(s,1H), 7.45(s,1H), 5.35(s,2H), 4.48(s,2H), 4.36(q,2H), 4.28(q,2H), 1.41(t,3H), 1.34(t,3H).

ii) 1-[[3-[[5-{5H-Dibenzo[a,d]cyclohepten-5-yl}-3,4dihydro-2,4-dioxo-1(2H)-pyrimidinyl]methyl]-5-[ethoxycarbonyl]phenyl]methyl]-4-pyrazolecarboxylic acid, ethyl ester The subtitle compound was prepared from the product of step (i) (0.79 g) and example 2 step (ii) (1.2 g) by the method of example 2 step (iii). Yield 0.72 g.

MS: APCI(+ve): 617(M+1, 100%)

iii) 1-[[3-[[5-{5H-Dibenzo[a,d]cyclohepten-5-yl}-3,4-dihydro-2-oxo-4-thioxo-1(2H)-pyrimidinyl]methyl]-5-[ethoxycarbonyl]phenyl]methyl]-4-pyrazolecarboxylic acid, ethyl ester The subtitle compound was prepared from the product of step (ii) (0.71 g) by the method of example 6 step (iv). Yield 0.33 g.

MS: APCI(+ve): 633 (M+1, 100%)

iv) 1-[[3-[[3-Carboxy-5-{5H-dibenzo[a,d]cyclohepten-5-yl}3,4-dihydro-2-oxo-4-thioxo-1(2H)-pyrimidinyl]methyl] phenyl]methyl]-4-pyrazolecarboxylic acid The title compound was prepared from the product of step (iii) (0.32 g) by the method of example 1 step (vi). Purified by reverse phase HPLC. Yield 0.03 g.

MS: APCI(+ve): 577 (M+1, 100%)

1H NMR δ (DMSO) 12.64(s,1H), 8.50(s, 1H), 7.90(s, 1H), 7.87(s,1H), 7.76(s,1H), 7.59-7.22(m,9H), 6.91(s,1H), 6.61(s,2H), 5.78(s,1H), 5.49(s,2H), 4.87(s,2H).

MP: 210–212° C.

Example 11

3-[[3-[[3Carboxy-5-{5H-Dibenzo[a,d]cyclohepten-5yl}-3,4-dihydro-2-oxo-4-thioxo-1(2H)-pyrimidinyl] methyl]phenyl]methoxy]-5ethoxybenzoic acid i) 3 Ethoxy-5-hydroxybenzoic acid, methyl ester Sodium hydride (1.19 g) was added to an ice-cold solution of methyl 3,5-dihydroxybenzoate (5 g) in dimethylformamide. The mixture was stirred at room temperature for 1 hour. Ethyl iodide (2.67 ml) was added and the mixture was stirred for 16 hours. The mixture was evaporated and the residue partitioned between ethyl acetate and by chromatography eluting with 25% ethyl acetate in isohexane. Yield 2.03 g.

MS: GC-MS: 196 (M+)

ii) 3-[[3-Bromomethyl-5-[ethoxycarbonyl]phenyl]methoxy]-5-ethoxybenzoic acid, methyl ester Sodium hydride (0.45 g) was added to a solution of the product from step (i) (2 g) in dimethylformamide (30 ml) with ice-cooling, 3,5-Bis[bromomethyl]benzoic acid ethyl ester (3.42 g) was added and the mixture was stirred for 16 hours. The solvent was evaporated and the residue partitioned between ethyl acetate and water. The organic phase was washed with water, dried (MgSO$_4$) and evaporated, Purified by chromatography eluting with 25% ethyl acetate in isohexane. Yield 1.21 g of a mixture (60% product, 40% dimer by $^1$H NMR). Used directly in the next step.

iii) 3-[[3-[[5-{5H-Dibenzo[a,d]cyclohepten-5-yl}-3,4-dihydro-2,4-dioxo-1-(2H)-pyrimidinyl]methyl]-5-[ethoxycarbonyl]phenyl]methoxy]-5-ethoxybenzoic acid, methyl ester The subtitle compound was prepared from the product of step (ii) (1.64 mmol) and example 2 step (ii) (0.49 g) by the method of example 7 step (ii). Purification was by chromatography eluting with 50% ethyl acetate in isohexane. Yield 0.7 g.

MS: APCI(+ve): 673 (M+1, 100%)

iv) 3-[[3-[[5-{5H-dibenzo[a,d]cyclohepten-5-yl}-3,4-dihydro-2-oxo-4-thioxo-1(2H)-pyrimidinyl]methyl]-5-[ethoxycarbonyl]phenyl]methoxy]-5-ethoxybenzoic acid, methyl ester The subtitle compound was prepared from the product of step (iii) (0.7 g) by the method of example 6 step (iv). Purification was by chromatography eluting with 25% ethyl acetate in isohexane. Yield 0.6 g.

MS: APCI(+ve): 689 (M+1, 100%)

v) 3-[[3-Carboxy-5-[[5-{5H-dibenzo[a,d]cyclohepten-5-yl}-3,4dihydro-2-oxo-4-thioxo-1(2H)-pyrimidinyl]methyl]phenyl]methoxy]-5-ethoxybenzoic acid The title compound was prepared from the product of step (iv) (0.6 g) by the method of example 1 step (vi). Yield 0.1 g.

MS: APCI(+ve): 647 (M+1, 100%)

1H NMR δ (DMSO) 8.05(s,1H), 7.81(s, 1H), 7.58(m,3H), 7.40-7.20(m,8H), 7.09(s,1H), 6.99(s,1H), 6.85(s,1H), 6.71 (s,2H), 5.79(s,1H), 5.25(s,2H), 4.90(s,2H), 4.07(q,2H), 1.33 (t,3H).

MP: 180–183° C.

Example 12

3-[[3-Carboxy-5-[[5-{5H-dibenzo[a,d]cyclohepten-5-yl}-3,4dihydro-2-oxo-4-thioxo-1(2H)-pyrimidinyl] methyl]phenyl]methoxy]-5-[2-methoxyethoxy]benzoic acid i) 3-Hydroxy-5-[phenylmethoxy]benzoic acid, methyl ester The subtitle compound was prepared from methyl 3,5-dihydroxybenzoate (5 g) and benzyl bromide (3.6 ml) by the method of example 11 step (i). Purification was by chromatography eluting with 30% ethyl acetate in isohexane. Yield 2.31 g.

MS: GC-MS: 258 (M+)

ii) 3-[2-Methoxyethoxy]-5-[phenylmethoxy]benzoic acid, methyl ester

The subtitle compound was prepared from the product of step (i) (2.31 g) and 2-bromoethyl methyl ether 90.92 ml) by the method of example 11 step (i). Yield 2.74 g.

MS: GC-MS: 316 (M+)

iii) 3-Hydroxy-5-[2-methoxyethoxy]benzoic acid, methyl ester

The product from step (ii) (2.74 g) was reduced by catalytic hydrogenation at 1 at. for 16 hours in ethyl acetate solution with 10% palladium on charcoal. Yield 1.5 g.

MS: GC-MS: 226 (M+)

iv) 3-[[3-Bromomethyl-5-[ethoxycarbonyl]phenyl]methoxy]-5-[2-methoxyethoxy]benzoic acid, methyl ester The subtitle compound was prepared from the product of step (iii) (1.5 g) and 3,5-bis(bromomethyl)benzoic acid ethyl ester (4.9g) by the method of example 11 step (i). Purification was by chromatography eluting with 30% ethyl acetate in isohexane. Yield 1.6 g. Used directly in the next step v) 3-[[3-[[5-{5H-Dibenzo[a,d]cyclohepten-5-yl}-3,4dihydro-2,4-oxo-4-dioxo-1(2H)-pyrimidinyl]methyl]-5-[ethoxycarbonyl]phenyl]methoxy]-5-[2-methoxyethoxy]benzoic acid, methyl ester The subtitle compound was prepared from the product of step (iv) (1.6 g) and example 2 step (ii) (1 g) by the method of example 7 step (ii). Purification was by chromatography eluting with 50% ethyl acetate in isohexane. Yield 1.47 g.

MS: APCI(+ve): 703 (M+1, 100%)

vi) 3-[[3-[[5-{5-Dibenzo[a,d]cyclohepten-5-yl}-3,4dihydro-2-oxo-4-thioxo-1(2H)-pyrimidinyl]methyl]-5-[ethoxycarbonyl]phenyl]methoxy]-5-[2-methoxyethoxy]benzoic acid, methyl ester The subtitle compound was prepared from the product of step (v) (1.5 g) by the method of example 6 step (iv). Purification was by chromatography eluting with 50% ethyl acetate in isohexane. Yield 0.37 g.

MS: APCI(+ve) 719 (M+1, 100%)

vii) 3-[[3-Carboxy-5-[[5-{5H-dibenzo[a,d]cyclohepten-5-yl}-3,4dihydro-2-oxo-4-thioxo-1(2H)-pyrimidinyl]methyl]phenyl]methoxy]-5-[2-methoxyethoxy]benzoic acid The title compound was prepared from the product of step (vi) (0.37 g) by the method of example 1 step (vi). Yield 0.23 g.

MS: APCI(+ve): 677(M+1, 100%)

1H NMR δ (DMSO) 8.03(s,1H), 7.79(s, 1H), 7.57(d,2H), 7.46(s,1H), 7.40-7.10(m,12H), 6.98(s,1H), 6.80(s,1H), 6.72 (s,2H), 5.79(s,1H), 5.20(s,2H), 4.87(s,2H), 4.12(br s,2H), 3.65(br s,2H), 3.30(s,3H).

Example 13

3-[[5-{5-H-Dibenzo[a,d]cyclohepten-5-yl}-3,4-dihydro-2-oxo-4thioxo-1(2H)-pyrimidinyl]methyl]-5-[hydroxymethyl]benzoic acid i) 3-Acetoxymethyl-5-[bromomethyl]benzoic acid, ethyl ester To a stirred solution of 18-crown-6 (0.103 g) in acetonitrile (15 ml) was added potassium acetate (0.38 g). After 30 minutes 3,5-bis[bromomethyl]benzoic acid ethyl ester (2.61 g) was added and the mixture was stirred overnight. The mixture was partitioned between ethyl acetate and water. The organic phase was dried (MgSO$_4$) and evaporated and the residue purified by chromatography eluting with 10% ethyl acetate in isohexane. Yield 0.97 g.

MS: GC-MS: 314/316 (M+)

ii) 3-[Acetoxymethyl]-5-[[5-{5H-dibenzo[a,d]cyclohepten -5-yl}-3,4-dihydro-2,4-dioxo-1(2H)-pyrimidinyl]methyl]benzoic acid, ethyl ester The subtitle compound was prepared from the product of step (i) (0.92 g) and example 2 step (ii) (0.88g) by the method of example 2 step (iii). Purification was by chromatography eluting with 40% ethyl acetate in toluene. Yield 0.92 G.

1H NMR δ (DMSO) 11.25(s,1H), 7.95(s, 1H), 7.75(s,1H), 7.53(d,2H), 7.48(s,1H), 7.38-7.33(m,2H), 7.31-7.23(m,5H), 6.71(s,2H), 6.67(s,1H), 5.32(s,1H), 5.18(s,2H), 4.84(s,2H), 4.39(q,2H), 2.11(s,3H), 1.37(t,3H).

Example 14

3-[[5-{5-H-Dibenzo[a,d]cyclohepten-5-yl}-3,4-dihydro-2-oxo-4thioxo-1(2H)-pyrimidinyl]methyl]-5-methylbenzoic acid i) 3-Bromomethyl-5-methylbenzoic acid, ethyl ester The subtitle compound was prepared from ethyl 3,5-dimethylbenzoate (2 g) and N-bromosuccinimide (2 g) by the method of example 5 step (i). Purification was by chromatography eluting with 5% ethyl acetate in isohexane Yield 1.85 g.

1H NMR δ (CDCl$_3$), 7.86(s,1H), 7.79(s,1H), 7.40(s,1H), 4.49(s,2H), 4.37(q,2H), 2.40(s,3H), 1.40(t,3H).

ii) 3-[[5-{5-H-Dibenzo[a,d]cyclohepten-5-yl}-3,4-dihydro-2-dioxo-1(2H)-pyrimidinyl]methyl]-5-methylbenzoic acid, ethyl ester The subtitle compound was prepared from the product of step (i) (0.85 g) and example 2 step (ii) (1 g) by the method of example 2 step (iii). Purification was by chromatography eluting with 25% ethyl acetate in isohexane. Yield 0.85 g.

1H NMR δ (CDCl$_3$) 8.55(s,1H), 7.88(s, 1H), 7.65(s,1H), 7.51(s,1H), 7.49(s,1H), 7.38-7.33(td,2H), 7.27-7.16(m,4H), 6.57(s,2H), 6.54(s,1H), 5.32(s,1H), 4.69(s,2H), 4.48-4.42(q, 2H), 2.42(s,3H), 1.48-1.44(t,3H).

iii) 3-[[5-{5-H-Dibenzo[a,d]cyclohepten-5-yl}-3,4-dihydro-2-oxo-4-thioxo-1(2H)-pyrimidinyl]methyl]-5-methylbenzoic acid, ethyl ester The subtitle compound was prepared from the product of step (ii) (0.85 g) by the method of example 5 step (iii). Purification was by chromatography eluting with 20% ethyl acetate in toluene. Yield 0.41 g.

1H NMR δ (DMSO) 12.63(s,1H), 7.81(s, 1H), 7.67(s, 1H), 7.58(d,2H), 7.36-7.23(m,7H), 6.94(s,1H), 6.78(s,2H), 5.80(s,2H), 4.84(s,2H), 4.38(q,2H), 2.41(s,3H), 1.37(t,3H).

iv) 3-[[5-{5-H-Dibenzo[a,d]cyclohepten-5-yl}-3,4-dihydro-2-oxo-4-thioxo-1(2H)-pyrimidinyl]methyl]-5-methylbenzoic acid The title compound was prepared from the product of step (iii) (0.412 g) by the method of example 1 step (vi). Purified by reverse phase HPLC. Yield 0.128 g.

MS: APCI(+ve): 467 (M+1, 100%)

1H NMR δ (DMSO) 7.78(s,1H), 7.65(s, 1H), 7.59-7.57 (d,2H), 7.36-7.20(m,7H), 6.96(s,1H), 6.72(s,2H), 5.80(s, 1H), 4.81(s,2H), 2.38(s,3H). 6.94(s,1H), 6.78(s,2H), 5.80(s, 2H), 4.84(s,2H), 4.38(q,2H), 2.41(s,3H), 1.37(t,3H).

MP:>240° C.

Example 15

5-[[5-{5-H-Dibenzo[a,d]cyclohepten-5-yl}-3,4-dihydro-2-oxo-4thioxo-1(2H)-pyrimidinyl]methyl]-2-hydroxybenzoic acid i) 2-Hydroxy-5-methylbenzoic acid, methyl ester To a solution of 5-methylsalicylic acid (7.24 g) in methanol (250 ml) was added trimethylsilyl chloride (60 ml). The mixture was heated at reflux for 2 hours and stirred at room temperature overnight. A further 60 ml trimethylsilyl chloride was added and the mixture heated at reflux for 6 hours. The mixture was evaporated and the residue partitioned between ethyl acetate and saturated aqueous sodium bicarbonate. The organic phase was dried (MgSO$_4$) and evaporated to give the crude product. Yield 5.87 g. Used directly in the next step.

ii) 2Acetoxy-5-methylbenzoic acid, methyl ester

A solution of the product from step (i) (5.87 g) in acetic anhydride (4.32 g) was treated with concentrated sulphuric acid (0.5 ml) and stirred for 72 hours. The mixture was poured into ice-water and extracted with diethyl ether. The extract was washed with water and saturated aqueous sodium bicarbonate, dried (MgSO$_4$) and evaporated. Yield 5.5 g.

1 H NMR: δ (CDCl$_3$), 8.04(d,1H), 7.58(dd,1H), 7.09(d, 1H), 4.49(s,2H), 3.88(s,3H), 2.35(s,3H).

iii) 2-Acetoxy-5-[bromomethyl]benzoic acid, methyl ester The subtitle compound was prepared from the product of step (ii) (2 g) by the method of example 5 step (i). Purification was by chromatography eluting with 5% ethyl acetate in isohexane. Yield 1.7 g.

1H NMR: δ (CDCl$_3$) 8.04(d,1H), 7.58(dd,1H), 7.09(d, 1H), 4.49(s,2H), 3.88(s,3H), 2.35(s,3H).

iv) 2-Acetoxy-5-[[5-{5H-dibenzo[a,d]cyclohepten-5-yl}-3,4-dihydro-2,4-dioxo-1(2H)-pyrimidinyl]methyl]benzoic acid, methyl ester The subtitle compound was prepared from the product of step (iii) (1.66 g) and example 2 step (ii) (1.75 g) by the method of example 2 step (iii). Purification was by chromatography eluting with 30% ethyl acetate in isohexane. Yield 1.05 g.

1H NMR δ (DMSO) 11.27(s,1H), 7.77(d,1H), 7.77-7.48 (m,3H), 7.38-7.23(m,5H), 7.18-7.12(m,2H), 6.77(s,2H), 6.63(s,1H), 5.31(s,1H), 4.82(s,2H), 3.88(s,3H), 2.33(s,3H).

v)2-Acetoxy-5-[[5-{5H-dibenzo[a,d]cyclohepten-5-yl}-3,4-dihydro-2-oxo-4-thioxo-1(2H)-pyrimidinyl]methyl] benzoic acid, methyl ester The subtitle compound was prepared from the product of step (iv) (1.05 g) by the method of example 6 step (iv). Purification was by chromatography eluting with 10–20% ethyl acetate in toluene. Yield 0.74 g.

MS: APCI(+ve): 525 (M+1, 100%)

vi) 5-[[5-{5-H-Dibenzo[a,d]cyclohepten-5-yl}-3,4-dihydro-2-oxo-4thioxo-1(2H)-pyrimidinyl]methyl]-2-hydroxybenzoic acid The title compound was prepared from the product of step (v) (0.64 g) by the method of example 1 step (vi). Purified by reverse phase HPLC. Yield 0.121 g.

MS: ESI-: 467 (M+1, 100%)

1H NMR δ (DMSO) 11.50(br s,1H), 7.62(d,1H), 7.55(d, 2H), 7.29-7.25(m,6H), 7.00(dd,1H), 6.92(s,1H), 6.73(s,2H), 6.73-6.65(d,1H), 5.81(s,1H), 4.62(s,2H).

MP:>240° C.

Example 16

[3-[[5-{5-H-Dibenzo[a,d]cyclohepten-5-yl}-3,4-dihydro-2-oxo-4thioxo-1(2H)-pyrimidinyl]methyl] phenoxy]acetic acid i) [3-Methylphenoxy]acetic acid, methyl ester A mixture of m-cresol (10.8 g), methyl bromoacetate (15.3 g) and potassium carbonate (69 g) in dimethylformamide (200 ml) was stirred overnight and partitioned between ethyl acetate and water. The organic phase was washed with water, dried (MgSO$_4$) and evaporated. Purified by chromatography eluting with toluene. Yield 12.7 g.

1H NMR δ (CDCl$_3$) 7.17(t,1H), 6.82(d,1H), 6.74(s,1H), 6.70(dd,1H), 4.62(s,2H), 3.80(s,3H), 2.33(s,3H).

ii) [3-[Bromomethyl]phenoxy]acetic acid, methyl ester

The subtitle compound was prepared from the product of step (i) (12.7 g) by the method of example 5 step (i). Purified by chromatography eluting with 5% ethyl acetate in isohexane. Yield 11.4 g.

1H NMR δ (CDCl$_3$) 7.27(t,1H), 6.94(s,1H), 6.84(d,1H), 4.65(s,2H), 4.45(s,2H), 3.82(s,3H).

iii) [3-[[5-{5-H-Dibenzo[a,d]cyclohepten-5-yl}-3,4-dihydro-2,4-dioxo-1(2H)-pyrimidinyl]methyl]phenoxy]acetic acid, methyl ester The subtitle compound was prepared from the product of step (ii) (1.28 g) and example 2 step (ii) (1.5 g) by the method of example 2 step (iii). Purification was by chromatography eluting with 30% ethyl acetate in isohexane. Yield 1.0 g.

1H NMR δ (DMSO) 11.23(s,1H), 7.52(d,2H), 7.37-7.23 (m,7H), 6.92(dd,1H), 6.76-6.71(m,4H), 6.58(s,1H), 5.30(s, 1H), 4.81(s,2H), 4.71(s,2H), 3.72(s,3H).

iv) [3-[[5-{5-H-Dibenzo[a,d]cyclohepten-5-yl}-3,4-dihydro-2-oxo-4-thioxo-1(2H)-pyrimidinyl]methyl]phenoxy]acetic acid, methyl ester The subtitle compound was prepared from the product of step (iii) (1 g) by the method of example 6 step (iv). Purification was by chromatography eluting with 10–20% ethyl acetate in toluene. Yield 0.75 g.

MS: APCI(+ve): 497 (M+1, 100%)

v) [3-[[5-{5-H-Dibenzo[a,d]cyclohepten-5-yl}-3,4-dihydro-2-oxo-4-thioxo-1(2H)-pyrimidinyl]methyl]phenoxy]acetic acid The title compound was prepared from the product of step (iv) (0.61 g) by the method of example 1 step (vi). Purified by reverse phase HPLC. Yield 0.4 g.

MS: ESI(+ve): 483 (M+1, 100%)

1H NMR δ (DMSO) 7.57(d,2H), 7.35-7.22(m,7H), 6.89 (m,2H), 6.76(s,1H), 6.71(d,1H), 6.67(s,2H), 5.80(s,1H), 4.72(s,2H), 4.43(s,2H).

MP: 148–155° C.

Example 17

2Bromo-5-[[5-{5H-dibenzo[a,d]cyclohepten-5-yl}-3,4-dihydro-2-oxo-4-thioxo-1(2H)-pyrimidinyl] methyl]benzoic acid i) 2-Bromo-5-methylbenzoic acid, methyl ester A solution of 2-bromo-5-methylbenzoic acid (10 g) in trimethylsilyl chloride (30 ml) and methanol (100 ml) was stirred at room temperature overnight and evaporated. The residue was partitioned between ethyl acetate and sodium bicarbonate solution, dried (MgSO$_4$) and evaporated. Yield 10.1 g.

1H NMR δ (CDCl$_3$) 7.60(d,1H), 7.52(d,1H), 7.13(dd,1H), 3.92(s,3H), 2.33(s,3H).

ii) 2-Bromo-5-[bromomethyl]benzoic acid, methyl ester

The subtitle compound was prepared from the product of step (i) (1.75 g) by the method of example 5 step (i). Purified by chromatography eluting with 15% ethyl acetate in isohexane. Yield 1.9 g.

1H NMR δ (CDCl$_3$) 7.82(d,1H), 7.64(d,1H), 7.36(dd,1H), 4.44(s,2H), 3.94(s,3H).

iii) 2-Bromo-5-[[5-{5H-dibenzo[a,d]cyclohepten-5-yl}-3,4-dihydro-2,4-dioxo-1(2H)-pyrimidinyl]methyl]benzoic acid, methyl ester The subtitle compound was prepared from the product of step (ii) (1.85 g) and example 2 step (ii) (1.8 g) by the method of example 2 step (iii). Purification was by chromatography eluting with 30% ethyl acetate in toluene. Yield 1 g.

1H NMR δ (DMSO) 11.26(s,2H), 7.80(d,1H), 7.58(s,1H), 7.53(d,2H), 7.40-7.20(m,7H), 6.73(s,2H), 6.63(s,1H), 5.30 (s,1H), 4.78(s,2H), 3.93(s,3H).

iv) 2-Bromo-5-[[5-{5H-dibenzo[a,d]cyclohepten-5-yl}-3,4-dihydro-2-oxo-4-thioxo-1(2H)-pyrimidinyl]methyl] benzoic acid, methyl ester the subtitle compound was prepared from the product of step (iii) (1 g) by the method of example 5 step (iii). Purification was by chromatography eluting with 25% ethyl acetate in toluene. Yield 0.4 g.

1H NMR δ (DMSO) 12.65(s,1H), 7.82(d,1H), 7.66(s,1H), 7.58(d,2H), 7.40-7.10(m,7H), 6.90(s,1H), 6.72(s,2H), 5.79 (s,1H), 4.84(s,2H), 3.93(s,3H).

v) 2-Bromo-5-[[5-{5H-dibenzo[a,d]cyclohepten-5-yl}-3,4-dihydro-2-oxo-4-thioxo-1(2H)-pyrimidinyl]methyl] benzoic acid The title compound was prepared from the product of step (iv) (0.35 g) by the method of example 1 step (vi). Purified by reverse phase HPLC. Yield 0.22 g.

MS: APCI (+ve): 531/533

1H NMR δ (DMSO) 7.56(d,2H), 7.51(d,1H), 7.40-7.20 (m,7H), 6.97(d,1H), 6.88(s,1H), 6.80(s,2H), 5.77(s,1H), 4.74(s,2H).

MP: 170–185° C.

Example 18

5-[[5-{5-H-Dibenzo[a,d]cyclohepten-5-yl}-3,4-dihydro-2-oxo-4thioxo-1(2H)-pyrimidinyl]methyl]-2-[phenylmethyl]benzoic acid i) 5-[[5-{5-H-Dibenzo[a,d]cyclohepten-5-yl}-3,4-dihydro-2,4-dioxo-1(2H)-pyrimidinyl]methyl]-2-[phenylmethyl]benzoic acid, methyl ester A mixture of the product from example 17 step (iii) (1.5 g) tetrabenzyltin (4.1 g) (Tetrahedron, 1993, 49, 9089) and tetrakis(triphenylphosphine) palladium (0) (0.35 g) in dry toluene (15 ml) and dry dimethylformamide (7 ml) was heated at 105° C. for 72 hours. A further 0.4 g palladium catalyst was added and the mixture heated for 72 hours. The mixture was partitioned between ethyl acetate and water. The organic phase was dried (MgSO$_4$) and evaporated. Purified by chromatography eluting with 25% ethyl acetate in toluene. Yield 0.28 g.

MS: APCI (+ve): 541 (M+1)

ii) 5-[[5-{5-H-Dibenzo[a,d]cyclohepten-5-yl}-3,4-dihydro-2-oxo-4-thioxo-1(2H)-pyrimidinyl]methyl]-2-[phenylmethyl]benzoic acid, methyl ester The subtitle compound was prepared from the product of step (i) (0.28 g) by the method of example 6 step (iv). Purified by chromatography eluting with 15% ethyl acetate in toluene. Yield 0.19 g.

1H NMR δ (DMSO) 12.62(s,1H), 7.67(d,1H), 7.56(d, 2H), 7.50-7.10(m,13H), 6.88(s,1H), 6.52(s,2H), 5.78(s,1H), 4.82(s,2H), 4.35(s,2H), 3.85(s,3H).

iii) 5-[[5-{5-H-Dibenzo[a,d]cyclohepten-5-yl}-3,4-dihydro-2-oxo-4-thioxo-1(2H)-pyrimidinyl]methyl]-2-[phenylmethyl]benzoic acid the title compound was prepared from the product of step (ii) (0.2 g) by the method of example 1 step (vi). Yield 0.12 g.

MS: APCI(+ve): 543 (M+1, 100%)

1H NMR δ (DMSO) 13.18(br s,1H), 12.63(s,1H), 7.70 (d,1H), 7.56(d,2H), 7.45-7.20(m,13H), 6.91(s,1H), 6.56(s, 2H), 5.78(s,1H), 4.81(s,2H), 4.40(s,2H).

MP: 135° C.

Example 19

2-Butyl-5-[[5-{5H-dibenzo[a,d]cyclohepten-5-yl}-3,4-dihydro-2-oxo-4-thioxo-1(2H)-pyrimidinyl]methyl]benzoic acid i) 2-Butyl-5-[[5-{5H-dibenzo[a,d]cyclohepten-5-yl}-3,4-dihydro-2,4-dioxo-1-(2H)-pyrimidinyl]methyl]benzoic acid, methyl ester The subtitle compound was prepared from the product of example 17 step (iii) (1.5 g) and tetra-n-butyltin (9 ml) by the method of example 18 step (i). Purified by chromatography eluting with 30% ethyl acetate in toluene. Yield 0.6 g.

MS: APCI(+ve): 507 (M+1, 100%)

ii) 2-Butyl-5-[[5-{5H-dibenzo[a,d]cyclohepten-5-yl}-3,4-dihydro-2-oxo-4-thioxo-1(2H)-pyrimidinyl]methyl]benzoic acid, methyl ester The subtitle compound was prepared from the product of example 17 step (iii) (1.5 g) and tetra-n-butyltin (9 ml) by the method of example 18 step (i). Purified by chromatography eluting with 305 ethyl acetate in toluene. Yield 0.6 g.

MS: APCI(+ve): 507 (M+1, 100%)

iii) 2-Butyl-5-[[5-{5H-dibenzo[a,d]cyclohepten-5-yl}-3,4-dihydro-2-oxo-4-thioxo-1(2H)-pyrimidinyl]methyl]benzoic acid The title compound was prepared from the product of step (ii) (0.4 g) by the method of example 1 step (vi). Purified by reverse phase HPLC. Yield 0.05 g.

MS: APCI(+ve): 509 (M+1, 100%)

1H NMR δ (DMSO) 13.10(br s,1H), 12.62(s,1H), 7.65 (d,1H), 7.57(d,2H), 7.40-7.20(m,8H), 6.94(s,1H), 6.70(s, 2H), 5.80(s,1H), 4.80(s,2H), 2.95(m,2H), 1.55(m,2H), 1.35 (m,2H), 0.92(t,3H).

MP: 230° C.

Example 20

4-[5-{5H-Dibenzo[a,d]cyclohepten-5-yl}3,4-dihydro-2-oxo-4-thioxo-1(2H)-pyrimidinyl]benzoic acid i) 4-[5-{5H-Dibenzo[a,d]cyclohepten-5-yl}3,4-dihydro-2-oxo-4-thioxo-1(2H)-pyrimidinyl]benzoic acid, ethyl ester A mixture of the product of example 2 step (ii) (1.5 g), potassium carbonate (1.71 g) and ethyl 4-fluorobenzoate (0.835 g) in dimethylsulphoxide (20 ml) was heated at 100° C. for 20 hours. Cesium carbonate(1.6 g) was added and the mixture heated at 100° C. for 5 hours. The mixture was partitioned between ethyl acetate and water. The organic phase was dried (MgSO$_4$) and evaporated. Purified by chromatography 20–30% ethyl acetate in isohexane. Yield 0.72 g.

MS: APCI(+ve): 451 (M+1)

ii) 4-[5-{5H-Dibenzo[a,d]cyclohepten-5-yl}3,4-dihydro-2-oxo-4-thioxo-1(2H)-pyrimidinyl]benzoic acid, ethyl ester The subtitle compound was prepared from the product of ste (i) (0.7 g) by the method of example 6 step (iv). Purified by chromatography eluting with 20% ethyl acetate in isohexane. Used directly in the next step MS: APCI(+ve): 467 (M+1, 100%)

iii) 4-[5-{5H-Dibenzo[a,d]cyclohepten-5-yl}3,4-dihydro-2-oxo-4-thioxo-1(2H)-pyrimidinyl]benzoic acid The title compound was prepared from the product of step (ii) by the method of example 1 step (vi). Purified by reverse phase chromatography. Yield 0.085%

MS: APCI(+ve): 439 (M+1, 100%)

1H NMR δ (DMSO) 13.20(br s,1H), 12.80(br s,1H), 8.04(d,2H), 7.66(d,2H), 7.40(m,8H), 7.09(s,2H), 6.94(s, 1H), 5.90(s,1H).

MP: 320° C.

Example 21

4-[[5-{5-H-Dibenzo[a,d]cyclohepten-5-yl}-3,4-dihydro-2-oxo-4-thioxo-1(2H)-pyrimidinyl]methyl]phenyl-1,3-bis[oxyacetic acid]

i) (±)-5-[[2H-3,4,5,6-Tetrahydropyran-2-yl]oxymethyl]benzene-1,3-diol

A mixture of 3,5-dihydrozybenzyl alcohol (10 g), dihydropyran (6.5 ml) and tosic acid (0.4 g) in dimethylformamide (50 ml) was stirred at roo temperature for 24 hours. The mixture was partitioned between ethyl acetate and water. The organic phase was dried (MgSO$_4$and evaporated. Purified by chromatography eluting with 25% ethyl acetate i isohexane. Yield 12 g.

1H NMR δ (DMSO) 9.13(s,2H), 6.17(d,2H), 6.10(t,1H), 4.63(m,1H), 4.48(d,1H), 4.26(d,1H), 3.75(m,1H), 3.45(m, 1H), 1.70(m,2H), 1.5(m,4H).

ii) (±)-5-[[2H-3,4,5,6-Tetrahydropyran-2-yl]oxymethyl]phenyl-1,3-bis[oxyacetic acid], diethyl ester A mixture of the product from step (i) (12 g) ethyl bromoacetate (26.7 g) and potassium carbonate (27.8 g) in dry dimethylformamide (80 ml) was stirred at room temperature of 5 hours and partitioned between ethyl acetate and water. The organic phase was dried (MgSO$_4$) and evaporated. Purified by chromatography eluting with 15% ethyl acetate in isohexane. Yield 13.1 g.

1H NMR δ (CDCl$_3$) 6.57(d,2H), 6.42(t,1H), 4.71(d,1H), 4.66(m,1H), 4.59(s,4H), 4.43(d,1H), 4.27(q,4H), 3.95-3.85 (m,1H), 3.55(m,1H), 2.00-1.50(m,6H), 1.33(t,6H).

iii) 5-[Hydroxymethyl]phenyl-1,3-bis[oxyacetic acid], diethyl ester

A solution of the product from step (ii) (13.1 g) in acetic acid (20 ml), water (5 ml) and tetrahydrofuran (10 ml) was heated at 45° C. for 24 hours. The solution was evaporated, azeotroped with toluene and the residue purified by chromatography eluting with 30% ethyl acetate in isohexane. Yield 6 g.

MS: APCI(+ve): 313 (M+1)

iv) 5-[Bromomethyl]phenyl-1,3-bis[oxyacetic acid], diethyl ester A mixture of the product from step (iii) (0.33g) and phosphorous tribromide (0.033 ml) in dry benzene (5 ml) was heated at reflux for 16 hours. The supernatant was decanted and evaporated to give the product. Yield 0.35 g.

MS: CG-MS: 374/6 .

v) 5-[[5-{5-H-Dibenzo[a,d]cyclohepten-5-yl}-3,4-dihydro-2,4-dioxo-1(2H)-pyrimidinyl]methyl]phenyl-1,3-bis[oxyacetic acid], diethyl ester The subtitle compound was prepared from the product of step (iv) (1.02 g) and example 2 step (ii) (0.75 g) by the method of example 7 step (ii). Purification was by chromatography eluting with 40% ethyl acetate in isohexane. Yield 1.04 g.

MS: APCI(+ve): 597 (M+1)

vi) 5-[[5-{5-H-Dibenzo[a,d]cyclohepten-5-yl}-3,4-dihydro-2-oxo-4-thioxo-1(2H)-pyrimidinyl]methyl]phenyl-1,3-bis[oxyacetic acid], diethyl ester The subtitle compound was prepared from the product of step (v) (1 g) by the method of example 6 step (iv). Purification was by chromatography eluting with 30% ethyl acetate in isohexane. Yield 0.7 g.

MS: APCI(+ve): 613 (M+1, 100%)

vii) 5-[[5-{5-H-Dibenzo[a,d]cyclohepten-5-yl}-3,4-dihydro-2-oxo-4-thioxo-1(2H)-pyrimidinyl]methyl]phenyl-1,3-bis[oxyacetic acid]

The title compound was prepared from the product of step (vi) (0.7 g) by the method of example 1 step (vi). Purified by reverse phase HPLC. Yield 0.12 g.

MS: APCI(−ve): 555 (M−1, 100%)

1H NMR δ (DMSO) 7.56(d,2H), 7.35-7.21(m,6H), 6.86 (s,1H), 6.69(s,2H), 6.44(d,1H), 6.30(d,2H), 5.79(s,1H), 4.65 (s,2H), 4.44(s,4H).

Example 22

4-[3-[Carboxymethoxy]-5-[[5-{5H-dibenzo[a,d] cyclohepten-5-yl}-3,4-dihydro-2-oxo-4-thioxo-1 (2H)-pyrimidinyl]methyl]phenyl]oxybutanoic acid i) 2-[3-Hydroxy-5-[hydroxymethyl]phenyloxy]acetic acid, ethyl ester the subtitle compound was prepared from 3,5-dihydroxybenzyl alcohol (5 g) and ethyl bromoacetate (5.96 g) by the method of example 21 step (ii). Purified by chromatography eluting with 30% ethyl acetate in isohexane. Yield 1.6 g.

1H NMR δ (DMSO) 9.40(s,1H), 6.36(br s,1H), 6.30(br s,1H), 6.15(br s,1H), 5.10(t,1H), 4.67(s,2H), 4.29(d,2H), 4.16(q,2H), 1.21(t,3H).

ii) 4-[3-[[Ethoxycarbonyl]methoxy]-5-[hydroxymethyl] phenyloxy]butanoic acid, ethyl ester The subtitle compound was prepared from the product of step (i) (1.6 g) and ethyl 4-bromobutyrate (1.38 g) by the method of example 21 step (ii). Purified by chromatography eluting with 30% ethyl acetate in toluene. Yield 0.43 g.

1H NMR δ (CDCl$_3$) 6.55(br s,1H), 6.50(br s,1H), 6.40(br s,1H), 4.62(d,2H), 4.30(q,2H), 4.12(q,2H), 3.98(t,2H), 2.49 (t,2H), 2.10(m,2H), 1.70(t,1H), 1.35-1.20(m,6H).

iii) 4-[3-Bromomethyl-5-[[ethoxycarbonyl]methoxy] phenyloxy]butanoic acid, ethyl ester The subtitle compound was prepared from the product of step (ii) (0.42 g) by the method of example 21 step (iv). Yield 0.47 g.

1H NMR δ (CDCl$_3$) 6.57(br s,1H), 6.51(br s,1H), 6.40(br s,1H), 4.60(s,2H), 4.40(s,2H), 4.30(q,2H), 4.12(q,2H), 3.98 (t,2H), 2.50(t,2H), 2.13(m,2H), 1.35-1.20(m,6H).

iv) 4-[3-[[5-{5H-Dibenzo[a,d]cyclohepten-5-yl)-3,4-dihydro-2,4-dioxo-1-(2H)-pryimidinyl]methyl]-5-[[ethoxycarbonyl]methoxy]phenyloxy]butanoic acid, ethyl ester The subtitle compound was prepared from the product of step (iii) (0.45 g) and example 2 step (ii) (0.38 g) by the method of example 7 step (ii). Purified by chromatography eluting with 30% ethyl acetate in toluene. Yield 0.5 g.

MS: APCI(+ve): 625 (M+1, 100%)

v) 4-[3-[[5-{5H-Dibenzo[a,d]cyclohepten-5-yl}-3,4-dihydro-2-oxo-4-thioxo-1(2H)-pyrimidinyl]methyl]5-[[ethoxycarbonyl]methoxy]phenyloxy]butanoic acid, ethyl ester The subtitle compound was prepared from the product of step (iv) (0.47 g) by the method of example 6 step (iv). Yield 0.32 g.

MS: APCI(+ve): 641 (M+1, 100%)

vi) 4-[5-[Carboxymethoxy]-3-[[5-{5H-dibenzo[a,d] cyclohepten-5-yl}-3,4-dihydro-2-oxo-4-thioxo-1(2H)-pyrimidinyl]methyl]phenyloxy]butanoic acid The title compound was prepared from the product of step (v) (0.32 g) by the method of example 1 step (vi). Yield 0.199 g.

MS: APCI(+ve): 558 (M+1, 100%)

1H, NMR: δ (DMSO) 12.60(s, 1H), 7.57(d, 2H), 7.40–7.20(m, 6H) 6.70(s, 1H), 6.64(s,2H), 6.52(s, 1H), 6.39(s, 1H), 6.36(s, 1H), 5.80(s, 1H), 4.70(br s, 4H), 3.95(t, 2H), 2.43(t, 2H), 1.95(m, 2H).

MP: 104–109° C.

Example 23

3-[[3-[[5-{5H-Dibenzo[a,d]cyclohepten-5-yl}-3,4-dihydro-2-oxo-4-thioxo-1(2H)-pyrimidinyl]methyl]phenyl] [carboxymethyl]amino]-3-thioxobutanoic acid i) N-[3-Methylphenyl]glycine, ethyl ester A mixture of m-toluidine (10 g), ethyl bromoacetate (10.3 ml), sodium acetate (7.6 g) and water (5 ml in ethanol (50 ml) was stirred at room temperature overnight. The product was filtered off as the hydrobromide salt. Yield 11.6 g.

1H NMR: δ (DMSO) 6.95(t, 1H) 6.39–6.31(m, 3H), 5.89(t, 1H), 4.10(q, 2H), 3,85(d, 2H), 2.17(s, 3H), 1.19(t, 3H).

ii) 3-[[Ethoxycarbonylmethyl][3-methylphenyl]amino]-3-oxobutanoic acid, ethyl ester The product of step (i) (2.74 g) was partitioned between ethyl acetate and saturated aqueous sodium bicarbonate. The organic phase was washed with bicarbonate, dried (MgSO$_4$) and evaporated. The residue was dissolved in diethyl ether (100 ml) and triethylamine (1.5 ml) was added. Ethyl succinyl chloride (1.6 ml) was added dropwise and the mixture was stirred at room temperature for 2 hours, filtered and evaporated. Purified by chromatography eluting with 15% ethyl acetate in isohexane. Yield 2.63 g.

1H NMR: δ (CDCl$_3$) 7.27(m, 1H), 7.19(m, 3H), 4.34(s, 2H), 4.19(q, 2H), 4.11(q, 2H), 2.60(t, 2H), 2.43(t, 2H), 2.37(s, 3H), 1.27(t, 3H), 1.24(t, 3H).

iii) 3-[[3-[Bromomethyl]phenyl][ethoxycarbonylmethyl] amino]-3-oxobutanoic acid, ethyl ester A solution of the product from step (ii) (2.63 g) and N-bromosuccinimide (1.51 g) in ethyl acetate (80 ml) with catalytic azoisobutyronitrile was irradiated under a 500 W halogen lamp for 6 hours. The mixture was evaporated and the residue purified by chromatography eluting with 10–20% ethyl acetate in isohexane. Yield 1.55 g.

1H NMR: δ (CDCl$_3$) 7.44–7.30(m, 4H), 4.49(s, 2H), 4.35(s, 2H), 4.20(q, 2H), 4.11(q, 2H), 2.61(m, 2H), 1.27(t, 3H), 1.24(t, 3H).

iv) 3-[[3-[[5-{5H-Dibenzo[a,d]cyclohepten-5-yl}-3,4-dihydro-2,4-dioxo-1(2H)-pyrimidinyl]methyl]phenyl] [ethoxycarbonylmethyl]amino]-3-oxobutanoic acid, ethyl ester The subtitle compound was prepared from the product of step (iii) (1.2 g) and example 2 step (ii) (0.8 g) by the method of example 7 step (ii). Purification was by chromatography eluting with 2% methanol in dichloromethane. The product was then recrystallised from ethyl acetate in isohexane. Yield 1.18 g.

1H NMR: δ (DMSO) 11.24(s, 1H), 7.51(m, 3H), 7.40–7.16(m, 9H), 6.73(s, 2H), 6.62(s, 1H), 5.31(s, 1H), 4.78(s, 2H), 4.90(q, 2H), 4.09(q, 2H), 4.00(q, 2H), 2.45(m, 2H), 2.27(m, 2H), 1.17(t, 3H), 1.15(t, 3H).

v) 3-[[3-[[5-{5H-Dibenzo[a,d]cyclohepten-5-yl}-3,4-dihydro-2-oxo-4-thioxo-1(2H)-pyrimidinyl]methyl]phenyl][ethoxycarbonylmethyl]amino]-3-thioxobutanoic acid, ethyl ester The subtitle compound was prepared from the product of step (iv) (1.18 g) by the method of example 6 step (iv). Purification was by chromatography eluting with 5% ethanol in dicloromethane. Yield 0.6 g.

MS: APCI(+ve): 654 (M+1, 100%)

vi) 3-[[3-[[5-{5H-Dibenzo[a,d]cyclohepten-3-yl}-3,4-dihydro-2-oxo-4-thioxo-1(2H)-pyrimidinyl]methyl]phenyl][carboxymethyl]amino]-3-thioxobutanoic acid The title compound was prepared from the product of step (v) (0.6 g) by the method of example 1 step (vi). Yield 0.12 g.

MS: APCI(+ve): 598 (M+1, 100%)

1H NMR: δ (DMSO) 12.63(s, 1H), 7.59(m, 3H), 7.46(d, 1H), 7.39–7.19(m, 8H), 6.95(s, 1H), 6.73(s, 2H), 5.81(s, 1H), 4.86(s, 2H), 4.83(br, s,2H), 2.66(m, 2H), 2.66(m, 2H), 2.50(m, 2H).

MP: 175° C.

Example 24

N-[[3-[[5-{5H-Dibenzo[a,d]-cyclohepten-5-yl}-3,4-dihydro-2-oxo-4-thioxo-1(2H)-pyrimidinyl]methyl]phenyl]methyl]-N-[phenylmethoxycarbonyl]glycine i) N-[1,1-Dimethylethoxycarbonyl]glycine, methyl ester Di-tert-butyldicarbonate (9.8 g) was added to a suspension of glycine methyl ester hydrochloride (5 g) and triethylamine (7 ml) in tetrahydrofuran (60 ml). The mixture was stirred at room temperature for 18 hours and partitioned between ethyl acetate and 2M HCl. The organic phase was dried (MgSO$_4$) and evaporated. Purified by chromatography eluting with 20–30% ethyl acetate is isohexane. Yield 7.43 g.

1H NMR: δ (CDCl$_3$) 5.03 (br s, 1), 3.92(d, 2H), 3.76(s, 3H), 1.46(s, 9H).

ii) N-[[3-[Bromomethyl]phenyl]methyl]-N-[1,1-dimethylethoxylcarbonyl]glycine, methyl ester A solution of the product from step (i) (5 g) in tetrahydrofuran (10 ml) was added dropwise to a suspension of sodium hydride (1.1 g) in tetrahydrofuran (40 ml) at 0° C. The mixture was warmed to room temperature and stirred for 30 minutes then added dropwise to a solution of α,α'-dibromo-m-xylene (10.56 g) in tetrahydrofuran (40 ml). The mixture was stirred at room temperature for 2 hours, quenched with aqueous ammonium chloride and partitioned between ethyl and acetate and water. The organic phase was dried (MgSO$_4$) and evaporated. Purified by chromatography eluting with 10% ethyl acetate in isohexane. Yield 2.8 g.

1H NMR δ (CDCl$_3$) 7.32–7.15(m, 4H), 4.54+4.50(2H, rotamers, 4.48(s, 2H), 3.95+3.80(2H, rotamers), 3.71(s, 3H), 1.47(s, 9H).

iii) N-[[3-[[5-H-Dibenzo[a,d]cyclohepten-5-yl}-3,4-dihydro-2,4-dioxo-1(2H)-pyrimidinyl]methyl]phenyl]methyl]-N-[1,1-dimethylethoxycarbonyl]glycine, methyl ester The subtitle compound was prepared from the product of step (ii) (2.08 ) and example 2 step (ii) (1.75 g) by the method of example 7 step (ii). Purified by chromatography eluting with 50% ethyl acetate in isohexane. Yield 1.8 g.

1H NMR: δ (DMSO) 11.21 (s, 1H), 7.52–7.23(m, 10H), 7.06(s, 2H), 6.67+6.65(2xs, 2H, rotamers), 6.56(s, 1H), 5.29(s, 1H), 4.72(s, 2H), 4.47+4.41(2xs, 2H, rotamers), 3.95+3.87(2xs, 2H, rotamers), 3.65+3.64(2xs, 3H, rotamers), 1.38+1.30(2xs, 9H, rotamers).

iv) N-[[3-[[5-{5H-Dibenzo[a,d]cyclohepten-5-yl}-3,4-dihydro-2,4-dioxo-1(2H)-pyrimidinyl]methyl]phenyl]methyl]glycine, methyl ester A solution of the product of step (iii) (1.8 g) in trifluoroacetic acid (5 ml) and dichloromethane (30 ml) was stirred overnight at room temperature. Toluene was added and the mixture was evaporated. The residue was partitioned between ethyl acetate and saturated aqueous sodium bicarbonate. The organic phase was dried (MgSO$_4$) and evaporated.

MS: APCI(+ve): 494 (M+1)

v) N-[[3-[[5-{5H-Dibenzo[a,d]cyclohepten-5-yl}-3,4-dihydro-2,4-dioxo-1(2H)-pyrimidinyl]methyl]phenyl]methyl]-N-[phenylmethoxycarbonyl]glycine, methyl ester Benzyl chloroformate (0.145 ml) was added to a solution of the product of step (iv) (0.44 g) and triethylamine (0.17 ml) in dichloromethane (10 ml). The mixture was stirred at room temperature for 2 hours. Further aliquots of benzyl chloroformate (0.1 ml) and triethylamine (0.3 ml) were added after 2 and 4 hours. The mixture was stirred overnight and partitioned between ethyl acetate and water. The organic phase was dried (MgSO$_4$), evaporated and purified by chromatography eluting with 60% ethyl acetate in isohexane. Yield 0.47 g.

1H NMR: δ (CDCl$_3$) 7.97(s, 1H), 7.51–6.95(m, 3H), 5.31(s, 1H), 5.23(d, 2H), 4.68–4.59(m, 4H), 3.97+3.87(2xs, 2H, rotamers), 3.70+3.65(2xs, 3H, rotamers).

vi) N-[[3-[[5-{5H-Dibenzo[a,d]cyclohepten-5-yl}-3,4-dihydro-2-oxo-4-thioxo-1(2H)-pyrimidinyl]methyl]phenyl]methyl]-N-[phenylmethoxycarbonyl]glycine, methyl ester The subtitle compound was prepared from the product of step (v) (0.46 g) by the method of example 6 step (iv). Yield 0.4 g.

MS: APCI(+ve): 644 (M+1)

vii) N-[[3-[[5-{5H-Dibenzo[a,d]cyclohepten-5-yl}-3,4-dihydro-2-oxo-4-thioxo-1(2H)-pyrimidinyl]methyl]phenyl]methyl]-N-[phenylmethoxycarbonyl]glycine The title compound was prepared from the product of step (vi) (0.39 g) by the method of example 1 step (vi). Yield 0.15 g.

MS: APCI(+ve): 630 (M+1)

1H NMR: δ (DMSO) 12.86(br s, 1H), 12.62(s, 1H), 7.57(d, 2H), 7.43–7.10(m, 15H), 6.88+6.84(2xs, 1H, rotamers), 6.63+6.56(2xs, 2H, rotamers), 5.79(s, 1H), 5.15+5.12(2xs, 2H, rotamers), 4.78+4.73(2xs, 2H, rotamers), 4.55 (s, 2H), 3.93(s, 2H).

MP: 120° C.

Example 25

3-[[5-{5H-Dibenzo[a,d]cyclohepten-5-yl}-3,4-dihydro-2-oxo-4-thioxo-1(2H)-pyrimidinyl]methyl]-5-[[carboxymethyl][diphenylmethyl]amino]benzoic acid i) 3-[Chlorocarbonyl]-5-nitrobenzoic acid, methyl ester A mixture of methyl hydrogen-5-nitroisophthalate (50 g) and thionyl chloride (75 ml) was heated of reflux overnight, cooled and evaporated. The residue was recrystallised from light petroleum (b.p. 40–60° C.) and a trace of ethyl acetate. Yield 50 g. Used directly in the next step.

ii) 3-[Hydroxymethyl]-5-nitrobenzoic acid, methyl ester

A stirred solution of the product from step (i) (46.54 g) and sodium borohydride (13.01 g) in 1,4-dioxane (200 ml) was heated at reflux for 17 hours. The mixture was cooled and treated with triethylamine (27.9 ml), poured onto ice-water and extracted with ethyl acetate. The combined extracts were dried (MgSO$_4$) and evaporated. The product was recrystallised from isohexane. Yield 19.38 g.

1H NMR: δ (CDCl$_3$) 8.76(t, 1H), 8.57(d, 1H), 8.45(s, 1H), 4.89(s, 2H), 3.99(s, 3H).

iii) 3-Amino-5-[hydroxymethyl]benzoic acid, methyl ester

A mixture of the product from step (ii) (23.4 g), ammonium chloride (23 g) and iron powder (23 g) in methanol (200 ml) and water (200 ml) was heated at reflux for 1 hour. The mixture was filtered and concentrated under reduced pressure and the residue treated with saturated aqueous sodium bicarbonate and extracted with ethyl acetate. The extract was dried (MgSO$_4$) and evaporated. Yield 19.38 g.

MG: GC-MS: 181 (M$^+$)

iv) 3-[[Ethoxycarbonylmethyl]amino]-5-[hydroxymethyl]benzoic acid, methyl ester

The subtitle compound was prepared from the product of step (iii) (10 g) by the method of example 22 step (i). Purified by chromatography eluting with 50% ethyl acetate in isohexane. Yield 9.98 g.

MS: APCI(+ve): 268 (M+1, 100%)

v) 3-[[Ethoxycarbonylmethyl][diphenylmethyl]amino]-5-[hydroxymethyl]benzoic acid, methyl ester A mixture of the product from step (iv) (3 g), potassium carbonate (15.48 g) and bromodiphenylmethane (2.77 g) in dimethylformamide (100 ml) was heated at 50° C. for 24 hours. The mixture was partitioned between ethyl acetate and brine. The organic phase was dried (MgSO$_4$) and evaporated. Purified by chromatography eluting with 30% ethyl acetate in isohexane. Yield 0.51 g.

MS: APCI(+ve): 434 (M+1)

vi) 3-Chloromethyl-5-[[ethoxycarbonylmethyl][diphenylmethyl]amino]benzoic acid, methyl ester The product of step (v) (0.5 g) in tetrahydrofuran (20 ml) was treated with triphosgene (0.114 g) then pyridine (0.183 g). After 16 hours the reaction was evaporated and purified by chromatography eluting with 20% ethyl acetate in isohexane. Yield 0.4 g.

MS: APCI(+ve): 452 (M+1)

vii)3-[[5-{5H-Dibenzo[a,d]cyclohepten-5-yl}-3,4-dihydro-2,4-dioxo-1-(2H)-pyrimidinyl]methyl]-5-[[ethoxycarbonylmethyl][dipehenylmethyl]amino]benzoic acid, methyl ester The subtitle compound was prepared from the product of step (vi) (0.4 g) and example 2 step (ii) (1.75 g) by the method of example 2 step (iii). Purified by chromatography eluting with 20% ethyl acetate in toluene. Yield 0.49 g.

MS: APCI(+ve): 718 (M+1)

vii)3-[[5-{5H-Dibenzo[a,d]cyclohepten-5-yl}-3,4-dihydro-2-oxo-4-thioxo-1(2H)-pyrimidinyl]methyl]-5-[[ethoxycarbonylmethyl][diphenylmethyl]amino]benzoic acid, methyl ester The subtitle compound was prepared from the product of step (vii) (0.49 g) by the method of example 6 step (iv). Purified by chromatography eluting with 20% ethyl acetate in toluene. Yield 0.26 g. Used directly in the next step.

viii)3[[5-{5H-Dibenzo[a,d]cyclohepten-5-yl}-3,4-dihydro-2-oxo-4-thioxo-1(2H)- pyrimidinyl]methyl]-5-[[ethoxycarbonylmethyl][diphenylmethy]amino]benzoic acid, methyl ester The subtitle compound was prepared from the product of step (vii) (0.49 g) by the method of example 6 step (iv). Purified by chromatography eluting with 20% ethyl acetate in toluene. Yield 0.26 g. Used directly in the next step.

ix) 3-[[5-{5H-Dibenzo[a,d]cyclohepten-5-yl}-3,4-dihydro-2-oxo-4-thioxo-1(2H)-pyrimidinyl][diphenylmethyl]amino]benzoic acid The title compound was prepared from the product of step (viii) (0.26 g) by the method of example 1 step (vi). Yield 0.16 g.

MS: APCI(+ve): 692 (M+1)

1H NMR: δ (DMSO) 12.95(br s, 1H), 12.55(br s, 1H), 12.40–11.00(br s, 1H), 7.60(d, 2H), 7.40–7.20(m, 17H), 7.10(s, 1H), 6.94(br s, 1H), 6.81(s, 1H), 6.80(s, 2H), 6.22(s, 1H), 5.80(s, 1H), 4.75(s, 2H), 4.00(s, 2H).

MP: 210° C.

Example 26

3-[[5-{5H-Dibenzo[a,d]cyclohepten-5-yl}-3,4-dihydro-2-oxo-4-thioxo-1(2H)-pyrimidinyl]methyl]-5-[carboxymethylamino]benzoic acid A mixture of the methyl ester of 3-[[5-{5H-dibenzo[a,d]cyclohepten-5-yl}-3,4-dihydro-2-oxo-4-thioxo-1(2H)-pyrimidinyl]methyl]-5-[carboxymethylamino]benzoic acid (by-product from example 25 step (viii) (0.041 g) and lithium hydroxide (0.011 g) in methanol (5 ml) and water (5 ml) was stirred at room temperature for 3 days and heated at 50° C. for 24 hours. The mixture was concentrated under reduced pressure and purified by reverse phase HPLC. Yield 28 mg.

MS: APCI(+ve): 526 (M+1, 100%)

Example 27

2-[2-5-{5H-Dibenzo[a,d]cyclohepten-5-yl}-3,4-dihydro-2-oxo-4-thioxo-1(2H)-pyrimidinyl]ethoxy]benzoic acid i) 2-[2-Bromoethoxy]benzoic acid, methyl ester The subtitle compound was prepared from methyl salicylate (5 g) and 1,2-dibromoethane (30.67 g) by the method of example 21 step (ii). Purified by chromatography eluting with 10% ethyl acetate in isohexane. Yield 4.9 g.

1H NMR: δ (CDCl$_3$) 7.81(dd, 1H), 7.48(ddd, 1H), 7.04 (dt, 1H), 6.98(br d, 1H), 4.37(t, 2H), 3.90(s, 3H), 3.70(t, 2H).

ii) 2-[2-[5-{5H-Dibenzo[a,d]cyclohepten-5-yl}-3,4-dihydro-2,4-dioxo-1(2H)-pyrimidinyl]ethoxy]benzoic acid, methyl ester The subtitle compound was prepared from the products of step (i) (0.86 g) and example 2 step (ii) (1 g) by the method of example 2 step (iii). Purified by chromatography eluting with 40% ethyl acetate in toluene. Yield 0.41 g.

MS: ESI(+ve): 480 (M$^+$)

iii) 2-[2-[5-{5H-Dibenzo[a,d]cyclohepten-5-yl}-3,4-dihydro-2-oxo-4-thioxo-1(2H)-pyrimidinyl]ethoxy]benzoic acid, methyl ester The subtitle compound was prepared from the product of step (ii) (0.4 g) by the method of example 5 step (iii). Recrystallised from toluene. Yield 0.09 g.

MS; APCI(+ve): 497 (M+1)

iv) 2-[2-5-{5H-Dibenzo[a,d]cyclohepten-5-yl}-3,4-dihydro-2-oxo-4-thioxo-1(2H)-pyrimidinyl]ethoxy]benzoic acid The title compound was prepared from the product of step (iii) (0.087 g) by the method of example 1 step (vi). Yield 0.014 g.

1H NMR: δ (DMSO) 12.61(s, 1H), 12.55(br s, 1H), 7.70(d, 1H), 7.60(d, 2H), 7.50(t, 1H), 7.40–7.20(m, 7H), 7.09(m, 2H), 6.82(s, 2H), 5.85(s, 1H), 4.21(t, 2H), 4.01(t, 2H).

Example 28

2-[Carboxymethoxy]-6-2-5-{5H-dibenzo[a,d]cyclohepten-5-yl}-3,4-dihydro-2-oxo-4-thioxo-1(2H)-pyrimidinyl]ethoxy]benzoic acid i) 2,6-Dihydroxybenzoic acid, methyl ester The subtitle compound was prepared from 2,6-dihydroxybenzoic acid (25 g) by the method of example 17 step (i). Yield 10.33 g. Used directly in the next step.

ii) 2-Hydroxy-6-[methoxycarbonylmethoxy]benzoic acid, methyl ester

The subtitle compound was prepared from the product of step (i) (10 g) and methyl bromacetate (5.5 ml) by the method of example 11 step (i). Purified by chromatography eluting with 20% ethyl acetate in isohexane. Yield 3.68 g.

1H NMR: δ (CDCl₃) 11.51(s, 1H), 7.33(t, 1H), 6.67(d, 1H), 6.30(d, 1H), 4.67(s, 2H, 3.97(s, 3H), 3.82(s, 3H).

iii) 2-[2-Bromoethoxy]-6-methoxycarbonylmethoxy]benzoic acid, methyl ester

The subtitle compound was prepared from the product of step (ii) (3.6 g) and 1,2-dibromoethane (5.17 ml) by the method of example 21 step (ii). Purified by chromatography eluting with 20% ethyl acetate in isohexane. Yield 3.2 g.

1H NMR: δ (CDCl₃) 7.29(t, 1H), 6.60(d, 1H), 6.48(d, 1H), 4.66(s, 2H), 4.31(t, 2H), 3.98(s, 3H), 3.80(s, 3H), 3.60(t, 2H).

iv) 2-[2-5-H-Dibenzo[a,d]cyclohepten-5-yl}-3,4-dihydro-2,4-dioxo-1-(2H)-pyrimidinyl]ethoxy]-6-[methoxycarbonylmethoxy]benzoic acid, methyl ester The subtitle compound was prepared from the product of step (iii) (1.44 g) and example 2 step (ii) (1.25 g) by the method of example 2 step (iii). Purified by chromatography eluting with 30% ethyl acetate in toluene. Yield 0.83 g. Used directly in the next step.

v) 2-[2-[5-{5H-Dibenzo[a,d]cyclohepten-5-yl}-3,4-dihydro-2-oxo-4-thioxo-1(2H)-pyrimidinyl]ethoxy]-6-[methoxycarbonylmethoxy]benzoic acid, methyl ester The subtitle compound was prepared from the product of step (iv) (0.83 g) by the method of example 6 step (iv). Purified by chromatography eluting with 30% ethyl acetate in toluene.

Yield 0.19 g. Used directly in the next step.

vi) 3-[2-[5-{5H-Dibenzo[a,d]cyclohepten-5-yl}-3,4-dihydro-2-oxo-4-thioxo-1(2H)-pyrimidinyl]ethoxy]-2-[methoxycarbonyl]phenoxyacetic acid, methyl ester The subtitle compound was prepared from the product of step (v) (0.19 g) by the method of example 1 step (vi). Purified by reverse phase chromatography. Yield 0.092 g.

MS: APCI(+ve): 571 (M+1)

vii) 2-[Carboxymethoxy]-6-[2-[5-{5H-dibenzo[a,d]cyclohepten-5-yl}-3,4-dihydro-2-oxo-4-thioxo-1(2H)-pyrimidinyl]ethoxy]benzoic acid A mixture of the product from step (vi) (0.073 g) and sodium hydroxide (1 g) in methanol (20 ml) and water (20 ml) was heated at 60° C. overnight. The mixture was acidified with 2M HCl and extracted with ethyl acetate. The extract was evaporated and the residue purified by reverse phase chromatography. Yield 0.04 g.

MS: APCI(+ve): 557 (M+1)

1H NMR: δ (DMSO) 12.95(br s, 1H), 12.60(br s, 1H), 7.60(d, 2H), 7.40–7.20(m, 7H), 7.05(br s, 1H), 6.89(s, 2H), 6.60(d, 2H), 5.83(s, 1H).

MP: 187° C.

Example 29

4-[2-[5-{5H-Dibenzo[a,d]cyclohepten-5-yl}-3,4-dihydro-2-oxo-4-thioxo-1(2H)-pyrimidinyl]ethoxy]-1,3-benzenedioic acid i) 4-Hydroxy-1,3-benzenedioic acid, dimethyl ester A mixture of 4-hydroxyisophthalic acid (25 g) and trimethylsily chloride (100 ml) in methanol (200 ml) was heated at reflux for 4 hours. The mixture was evaporated and partitioned between ethyl acetate and aqueous sodium bicarbonate. The organic phase was dried (MgSO₄) and evaporated. Yield 25.67 g. Used directly in the next step.

ii) 4-[2-Bromoethoxy]-1,3-benzenedioic acid, dimethyl ester

A mixture of the product of step (i) (5 g) and potassium carbonate (13.14 g) in dimethylformamide (100 ml) was treated with 1,2-dibromoethane (8.2 ml) and stirred overnight at room temperature. The mixture was partitioned between ethyl acetate and water. The organic phase was dried (MgSO₄) and evaporated. Purified by chromatography eluting with 20% ethyl acetate in isohexane. Yield 4.6 g.

1H NMR: δ (CDCl₃) 8.49(s, 1H), 4.44(t, 2H), 3.95(s, 6H), 3.70(t, 2H).

iii) 4-2-[5-{5H- Dibenzo[a,d]cyclohepten-5-yl}-3,4-dihydro-2,4-dioxo-1(2H)-pyrimidinyl]ethoxy]-1,3-benzenedioic acid, dimethyl ester The subtitle compound was prepared from the product of step (ii) (1.31 g) and example 2 step (ii) (1.25 g) by the method of example 2 step (iii). Yield 0.83 g. Used directly in the next step.

iv) 4-2-{5H-Dibenzo[a,d]cyclohepten-5-yl}-3,4-dihydro-2-oxo-4-thioxo-1(2H)-pyrimidinyl]ethoxy]-1,3-benzenedioic acid, dimethyl ester The subtitle compound was prepared from the product of step (iii) (0.81 g) by the method of example 6 step (iv). Purified by chromatography eluting with 40% ethyl acetate in dichloromethane. Yield 0.34 g. Used directly in the next step.

v) 4-[2-[5-{5H-Dibenzo[a,d]cyclohepten-5-yl}-3,4-dihydro-2-oxo-4-thioxo-1(2H)-pyrimidinyl]ethoxy]-1,3-benzenedioic acid The title compound was prepared from the product of step (iv) (0.33 g) by the method of example 1 step (vi). Purified by reverse phase chromatography. Yield 0.095 g.

MS: APCI(+ve): 527 (M+1)

1H NMR: δ](DMSO) 12.88(br s, 1H), 12.61(s, 1H), 8.27(s, 1H), 8.05(d, 1H), 7.60(d, 2H), 7.30(m, 9H), 7.10(br s, 1H), 6.83(s, 2H), 5.84(s, 1H), 4.32(m, 2H), 4.04(m, 2H).

MP: 284° C.

Example 30

3-[[5-{5H-Dibenzo[a,d]cyclohepten-5-yl}-3,4-dihydro-2,4-dithioxo-1(2H)-pyrimidinyl]methyl]benzoic acid i) 3-[[5-{5H-Dibenzo[a,d]cyclohepten-5-yl}-4-methylthio-2-oxo-1(2H)-pyrimidinyl]methyl]benzoic acid, methyl ester A mixture of the product from example 2 step (iv) (1 g), sodium bicarbonate (0.22 g) and methyl iodide (0.7 ml) in water (4 ml) and methanol (30 ml) was heated at 40° C. for 4 hours. The mixture was concentrated under reduced pressure and partitioned between ethyl acetate and water. The organic phase was dried (MgSO$_4$) and evaporated. Used directly in the next step.

ii) 3-[[5-{5H-Dibenzo[a,d]cyclohepten-5-yl}-4-methylthio-2-thioxo-1(2H)-pyrimidinyl]methyl]benzoic acid, methyl ester The subtitle compound was prepared from the product of step (i) by the method of example 1 step (v) using benzene as solvent. Purified by chromatography eluting with 8% ethyl acetate in toluene. Yield 0.6 g.

1H NMR: δ (DMSO) 7.98(d, 1H), 7.78(s, 1H), 7.67(d, 2H), 7.59(t, 1H), 7.53(d, 1H), 7.45–7.40(m, 2H), 7.35–7.30 (m, 4H), 6.82(s, 1H), 6.62(s, 2H), 5.55(s, 2H), 5.47(s, 1H), 3.94(s, 3H), 2.36(s, 3H).

iii) 3-[[5-{5H-Dibenzo[a,d]cyclohepten-5yl}-3,4-dihydro-2,4-dithioxo-1(2H)-pyrimidinyl]methyl]benzoic acid, methyl ester Hydrogen sulphide gas was bubbled through a solution of the product from step (ii) (0.3 g) in triethylamine (10 ml) and pyridine (40 ml) at room temperature for 2 hours. The mixture was evaporated. Purified by chromatography eluting with 8% ethyl acetate in toluene.

Yield 0.28 g.

1H NMR: δ (DMSO) 13.73(s, 1H), 8.00(m, 1H), 7.85(s, 1H), 7.65–7.55(m, 3H), 7.40–7.30(m, 1H), 7.30–7.20(m, 6H), 6.97(s, 1H), 6.57(s, 2H), 5.97(s, 1H), 5.75(s, 1H), 5.41(s, 2H), 3.93(s, 3H).

iv) 3-[[5-{5H-Dibenzo[a,d]cyclohepten-5-yl}-3,4-dihydro-2,4-dithioxo-1(2H)-pyrimidinyl]methyl]benzoic acid The title compound was prepared from the product of step (iii) (0.28 g) by the method of example 1 step (vi). Yield 0.21 g.

MS: APCI(+ve): 469 (M+1, 100%)

1H NMR: δ (DMSO) 13.73(s, 1H), 13.18(br s, 1H), 8.00(d, 1H), 7.83(s, 1H), 7.70–7.50(m, 4H), 7.40–7.30(m, 2H), 7.30–7.20(m, 4H), 6.90(s, 1H), 6.60(s, 2H), 5.40(s, 2H).

MP: 167–170° C.

Example 31

3-[[5-{5H-Dibenzo[a,d]cyclohepten-5-yl}-3,4-dihydro-4-oxo-2-thioxo-1(2H)-pyrimidinyl]methyl]benzoic acid i) 3-Methylbenzoic acid, [1,1-dimethylethyl] ester To a solution of tert-butanol (12.2 ml) in tetrahydrofuran (300 ml) at 0° C. was added n-butyllithium (52 ml) dropwise over 10 minutes. m-Toluoyl chloride (20 g) was added and the mixture heated at reflux for 1 hours. The mixture was partitioned between ethyl acetate and water and the organic phase dried (MgSO$_4$) and evaporated. Purified by chromatography eluting with 20% dichloromethane in isohexane. Yield 14.78 g. Used directly in the next step.

ii) 3-[Bromomethyl]benzoic acid, [1,1-dimethylethyl] ester

The subtitle compound was prepared from the product of step (i) (14.78 g) by the method of example 23 step (iii). Purified by chromatography eluting with 10% ethyl acetate in isohexane. Yield 12.35 g.

1H NMR: δ (CDCl$_3$) 7.99(s, 1H), 7.93(d, 1H), 7.54(d, 1H), 4.52(s, 2H), 1.60(s, 9H).

iii) 3-[[5-{5H-Dibenzo[a,d]cyclohepten-5-yl}-3,4-dihydro-2,4-dioxo-1(2H)-pyrimidinyl]methyl]benzoic acid, [1,1-dimethylethyl] ester The subtitle compound was prepared from the product of step (ii) (4.3 g) and example 2 step (ii) (1.25 g) by the method of example 7 step (ii). Purified by chromatography eluting with 25% ethyl acetate in toluene. Yield 5.25 g.

1H NMR: δ (DMSO) 11.26(brs, 1H), 7.90(d, 1H), 7.72(s, 1H), 7.52(d, 2H), 7.50–7.20(m, 6H), 6.70(s, 2H), 6.68(brs, 1H), 5.31(s, 1H), 4.80(s, 2H), 1.58(s, 9H).

iv) 3-[[5-{5-H-Dibenzo[a,d]cyclohepten-5-yl}-3,4-dihydro-2-oxo-4-thioxo-1(2H)-pyrimidinyl]methyl]benzoic acid, [1,1]-dimethylethyl] ester The subtitle compound was prepared from the product of step (iii) (2 g) by the method of example 6 step (iv). Purified by chromatography eluting with 30% ethyl acetate in toluene.

Yield 1.96 g. Used directly in the next step.

v) 3-[[5-{5H-Dibenzo[a,d]cyclohepten-5-yl}-4-methylthio-2-oxo-1(2H)-pyrimidinyl]methyl]benzoic acid, [1,1-dimethylethyl] ester The subtitle compound was prepared from the product of step (iv) (0.5 g) by the method of example 30 step (i). Yield 0.46 g.

1H NMR: δ (CDCl$_3$) 8.03(m, 1H), 7.77(s, 1H), 7.50–7.10 (m, 9H), 6.47(s, 1H), 6.53(s, 2H), 4.87(s, 2H), 5.20(s, 1H), 2.44(s, 3H), 1.66(s, 9H).

vi) 3-[[5-{5H-Dibenzo[a,d]cyclohepten-5-yl}-4-methylthio-2-thioxo-1(2H)-pyrimidinyl]methyl]benzoic acid, [1,1-dimethylethyl] ester A mixture of the product from step (v) (0.46 g) and Lawesson's reagent (0.18 g) in benzene (5 ml) was heated at reflux for 2 hours. The mixture was evaporated and purified by chromatography eluting with 10% ethyl acetate in toluene. Yield 0.5 g.

MS: APCI(+ve): 539 (M+1, 100%)

vii) 3-[[5-{5H-Dibenzo[a,d]cyclohepten-5-yl}-3,4-dihydro-4-oxo-2-thioxo-1(2H)-pyrimidinyl]methyl]benzoic acid A solution of the product from step (vi) (0.5 g) in dichloromethane (12 ml) was treated with trifluoracetic acid (9 ml) and stirred at room temperature for 3.5 hours. The mixture was evaporated and the residue dissolved in ethanol (50 ml) and 2M HCl. The mixture was heated at reflux at 4 hours. The mixture was evaporated and the residue treated with water, filtered and dried (MgSO$_4$). Purified by chromatography eluting with 5% methanol in dichloromethane. Yield 0.27 g.

MS: APCI(−ve): 451 (M−1, 100%)

$^1$H NMR: δ (DMSO) 13.18(br s, 1H), 12.60(br s, 1H), 7.97(d, 1H), 7.78(s, 1H), 7.60–7.20(m, 10H), 6.73(s, 1H), 6.62(s, 2H), 5.39(s+s, 3H).

MP: 258° C.

PHARMACOLOGICAL DATA

The following example describes the assay used to determine how strongly the compounds of the invention bind to P-2-purinoceptor 7-TM G-protein coupled receptors. The assay used a human P2Y2 receptor clone which was isolated from HL60 cells cDNA and then stably transfected into a Jurkat cell line (using methods described in "Cloning and Characterisation of a Bovine P$_{2Y}$ Receptor" Henderson et al (1995), 212, 2, 648–656; Parr et al Proc. Natl. Acad. Sci USA (1994), 91, 3275–3279 and Proc Natl Acad Sci USA (1994), 91, 13067). The cloned receptor mediates an increase in intracellular calcium in the cell line, which possesses no endogenuous nucleotide receptor of its own.

The transfected Jurkat cells were maintained at a concentration of from about $1\times10^5$ to $10\times10^5$ cells/ml in RPMI containing 4% heat inactivated bovine serum, 2% penicillin/streptomycin and 1% glutamine. The cells were incubated at 37° C. in an atmosphere of air with 5% $CO_2$.

The cells were spun down at r.p.m. for 5 minutes and resuspended in 10 ml basal salt solution (BSS) containing 125 mM of NaCl, 5 mM of KCl, 1 mM of $MgCl$, 1.5 mM of $CaCl_2$, 25 mM of HEPES, 5 mM of glucose and 1 mg/ml of bovine serum albumin, having a pH of 7.3. The concentration of cells was determined using a Technicon cell counter. From $0.75\times10^8$ to $1\times10^8$ cells were spun down, resuspended to a concentration of $3.3\times10^7$ cells/ml in BSS and incubated with either 17 μM fluo-3AM or 17 μM Fura-2AM at 37° C. for 35 minutes with vigorous shaking. The dye used was dependent upon the fluorescence and absorption properties of the compounds of the invention. In general for compounds of formula (I) wherein $Q^1$ represents a S atom, fluo-3AM was used and for compounds wherein $Q^1$ represents an O atom, either fluo-3AM or fura-2 AM were used. The cells were again spun down and washed once with the same volume of BSS before being resuspended in BSS to a concentration of $1\times10^6$ cells/ml ready for testing.

When fluo-3AM was used as the dye, the cell solution was left at room temperature to recover for approximately 30 minutes before testing.

Fura-3AM loaded cells were divided into aliquots of about 10 ml and were warmed to 37° C. for 10 minutes before testing.

Calcium response were measured on a SPEX Fluomax using 508 nm excitation and 525 nm emission wavelengths at room temperature for Fluo-3 AM loaded cells and 340/380 nm excitation and 510 nm emission wavelengths for Fura-2 AM loaded cells. Each cuvette contained 2 ml of cells and was stirred at high speed throughout the test. Basal fluorescence was measured for 5 seconds before 20 μl of a $10^{-2}$–$10^{-6}$ M solution of the test compound in water was added to the 2 ml solution of the cells. The response was calibrated by the addition of Triton-X-100 (68 μl, 10% solution) and then EGTA (180 μl, 0.5 M solution). For each compound the response was compared to that of UTP.

The compounds exemplified have pA2 values greater than 4.0.

What is claimed is:
1. A compound of formula I:

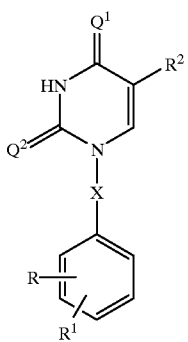

(I)

in which:

X is a bond, $CH_2$ or a $C_{1-3}$alkylene group optionally interrupted by oxygen;

R is hydrogen, $NO_2$, $NH_2$, $N(C_{1-6}alkyl)_2$, $CO_2H$, $CH_2OH$, halogen, $CO_2C_{1-6}$alkyl, $C_{1-8}$alkyl optionally interrupted by one or more oxygen, nitrogen or sulphur atoms and optionally substituted by $CO_2H$ or R is hydroxy, phenyl optionally substituted by $CH_2CO_2H$, or $CONR^3R^4$ where $R^3$ and $R^4$ are independently hydrogen, $C_{1-6}$alkyl optionally substituted by hydroxy or $CO_2H$ and/or optionally interrupted by oxygen, nitrogen or sulphur;

$R^1$ is $NR^5R^6$ or $CH_2NR^5R^6$ where $R^5$ and $R^6$ are independently hydrogen, $CH_2CO_2H$, $CHPh_2$ or $C(=S)CH_2CH_2CO_2H$, or $R^1$ is $CH_2NR^7CH_2CO_2H$ where $R^7$ is hydrogen, $C_{1-6}$ alkyl or $CO_2CH_2PH$, or $R^1$ is $C_{1-8}$alkyl optionally interrupted by one or more oxygen, nitrogen or sulphur atoms and optionally substituted by $CO_2H$, or $R^1$ is —$R^8$—$PO(OH)_2$, or —$R^8$-tetrazol-5-yl where $R^8$ is a bond, $OCH_2$, $SCH_2$, $CONH$, $CONHCH_2$, $CONHCH_2CONH$, $NHCH_2CONH$, $NHCH(R^3)$, $NR^9(CH_2)q$ where $R^9$ is hydrogen or $C_{1-6}$alkyl and q is 1 or 2 or $R^{20}$—$CO_2H$ where $R^{20}$ is a bond, $CONHCH_2$ or $NHCH(R^3)$ where $R^3$ is as defined above, or $R^1$ is a group of formula (i):

(i)

where B is a 4-, 5-, or 6-membered saturated ring containing a nitrogen atom optionally substituted by hydroxy and substituted by $CO_2H$ or CONH-Het where Het is tetrazol-5-yl, or a thiazole or thiadiazole ring substituted by $CO_2H$ or $CH_2CO_2H$, or B is phenyl or a 5-membered aromatic heterocylic ring containing 1 to 3 heteroatoms selected from nitrogen, oxygen or sulphur optionally substituted by one or more groups selected from $CF_3$, $CO_2H$, $CH_2OH$, $C_{1-6}$alkyl optionally interrupted by one or more oxygen atoms, $CH_2CH_2CO_2H$, $C(CO_2H)=N$—OMe, tetrazol-5-yl or $CH_2$tetrazol-5-yl; and $R^{10}$ is a bond, sulphur atom, —CONH—, $CH_2$, $CH_2O$, a group —$NR^{11}$—$CH(CO_2H)$—$CH_2$—, or a group or —$NR^{11}$—$(CH_2)_p$—$CONR^{12}$—where $R^{11}$ and $R^{12}$ are independently hydrogen or $C_{1-6}$alkyl and p is 1 or 2;

$R^2$ is a group of formula (ii) or (iii):

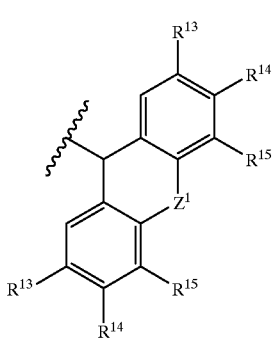

(ii)

-continued

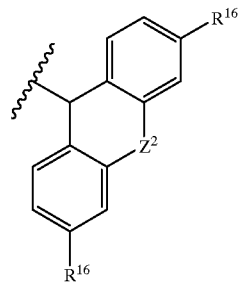

(iii)

where R$^{13}$ groups are independently hydrogen, halogen, methoxy, methylthio or C$_{1-2}$alkyl (optionally substituted by one or more fluorine atoms);

R$^{14}$ groups are independently hydrogen, halogen, hydroxy, C$_{1-3}$alkylthio, C$_{1-4}$alkyl (optionally substituted by one or more fluorine atoms, C$_{3-4}$ cycloalkyl, MeOCH$_2$, MeSCH$_2$ or C$_{1-2}$alkoxy;

R$^{15}$ groups are independently hydrogen, halogen or methyl (optionally substituted by one or more fluorine atoms);

Z$^1$ is CH=CH, CF=CH or CF=CF;

Z$^2$ is a single bond, oxygen, sulphur, CH$_2$CH=CH, CH$_2$CH=CHCH$_2$ or a C$_{1-4}$alkylene group optionally interrupted by an oxygen or sulphur atom;

R$^{16}$ are independently hydrogen, halogen, C$_{1-2}$alkyl, CF$_3$ or a methylthio group or hydroxy;

Q$^1$ and Q$^2$ each independently represent an O or S;

or a salt thereof, provided that when Q$^1$ is oxygen, R$^2$ is a group of formula (ii).

2. A compound according to claim 1 in which X is CH$_2$, a bond or CH$_2$CH$_2$O.

3. A compound according to claim 1 in which R is hydrogen, C$_{1-6}$alkoxy, C$_{1-8}$alkyl optionally interrupted by one or two oxygen atoms and optionally substituted by CO$_2$H, CH$_2$OH, hydroxy and halogen.

4. A compound according to claim 1 in which R$^1$ is CO$_2$H, —PO(OH)$_2$, C$_{1-8}$alkyl optionally interrupted by one or two oxygen atoms and optionally substituted by CO$_2$H, or R$^1$ is a group of formula (i) where B is phenyl, thiazole, pyrazole optionally substituted by CO$_2$H or C$_{1-6}$alkyl optionally interrupted by one or two oxygen atoms, or R$^1$ is NR$^5$R$^6$ or CH$_2$NR$^5$R$^6$ where R$^5$ and R$^6$ are independently, CH$_2$CO$_2$H, CHPh$_2$ or C(=S)CH$_2$CH$_2$CO$_2$H—, or R$^1$ is CH$_2$NR$^7$CH$_2$CO$_2$H where R$^7$ is CO$_2$CH$_2$Ph.

5. A compound according to claim 1 in which R$^2$ is a group of formula (ii) where Z$^1$ is CH=CH.

6. A compound according to claim 1 in which Q$^1$ is S and Q$^2$ is O or S.

7. A compound according to claim 1 which is:

3-[[5-[9H-Fluoren-9-yl]-3,4-dihydro-2-oxo-4-thioxo-1 (2H)-pyrimidinyl]methyl]benzoic acid, 3-[[5-{5H-Dibenzo[a,d]cyclohepten-5-yl}-3,4-dihydro-2-oxo-4-thioxo-1(2H)-pyrimidinyl]methyl]benzoic acid, 3-[[5-{5H-Dibenzo[a,d]cyclohepten-5-yl}-3,4-dihydro-2-oxo-4-thioxo-1(2H)-pyrimidinyl]methyl]benzeneacetic acid, 3-[[5-{5H-Dibenzo[a,d]cyclohepten-5-yl}-3,4-dihydro-2-oxo-4-thioxo-1(2H)-pyrimidinyl]methyl]benzenephosphonic acid, 5-[[5-{5H-Dibenzo[a,d]cyclohepten-5-yl}-3,4-dihydro-2-oxo-4-thioxo-1(2H)-pyrimidinyl]methyl]-2-methoxybenzoic acid, 2-[3-[[5-{5H-Dibenzo[a,d]cyclohepten-5-yl}-3,4-dihydro-2-oxo-4-thioxo-1-(2H)-pyrimidinyl]methyl]phenyl]-4-thiazolecarboxylic acid, 3-[[5-{5H-Dibenzo[a,d]cyclohepten-5-yl}-3,4-dihydro-2-oxo-4-thioxo-1(2H)-pyrimidinyl]methyl]-5-[2-methoxyethoxymethyl]benzoic acid, 3-[[5-{5H-Dibenzo[a,d]cyclohepten-5-yl}-3,4-dihydro-2-oxo-4-thioxo-1(2H)-pyrimidinyl]methyl]-5-[phenoxymethyl]benzoic acid, 3-[[5-{5H-Dibenzo[a,d]cyclohepten-5-yl}-3,4-dihydro-2-oxo-4-thioxo-1(2H)-pyrimidinyl]methyl]-5-[ethoxymethyl]benzoic acid, 1-[[3-[[3-Carboxy-5-{5H-dibenzo[a,d]cyclohepten-5-yl}-3,4-dihydro-2-oxo-4-thioxo-1(2H)-pyrimidinyl] methyl]phenyl]methyl]-4-pyrazolecarboxylic acid, 3-[[3-[[3-Carboxy-5-{5H-dibenzo[a,d]cyclohepten-5-yl}-3,4-dihydro-2-oxo-4-thioxo-1(2H)-pyrimidinyl] methyl]phenyl]methyl]-5-ethoxybenzoic acid, 3-[[3-Carboxy-5-[[5-{5H-dibenzo[a,d]cyclohepten-5-yl}-3,4-dihydro-2-oxo-4-thioxo-1(2H)-pyrimidinyl] methyl]phenyl]methoxy]-5-[2-methoxyethoxy]benzoic acid, 3-[[5-{5H-Dibenzo[a,d]cyclohepten-5-yl}-3,4-dihydro-2-oxo-4-thioxo-1(2H)-pyrimidinyl]methyl]-5-[hydroxymethyl]benzoic acid, 3-[[5-{5H-Dibenzo[a,d]cyclohepten-5-yl}-3,4-dihydro-2-oxo-4-thioxo-1(2H)-pyrimidinyl]methyl]-5-[methylbenzoic acid, 5-[[5-{5H-Dibenzo[a,d]cyclohepten-5-yl}-3,4-dihydro-2-oxo-4-thioxo-1(2H)-pyrimidinyl]methyl]-2-hydroxybenzoic acid, 3-[[5-{5H-Dibenzo[a,d]cyclohepten-5-yl}-3,4-dihydro-2-oxo-4-thioxo-1(2H)-pyrimidinyl]methyl]phenoxy] acetic acid, 2-Bromo-5-[[5-{5H-Dibenzo[a,d]cyclohepten-5-yl}-3,4-dihydro-2-oxo-4-thioxo-1(2H)-pyrimidinyl]methyl] benzoic acid, 5-[[5-{5H-Dibenzo[a,d]cyclohepten-5-yl}-3,4-dihydro-2-oxo-4-thioxo-1(2H)-pyrimidinyl]methyl]-2-[phenylmethyl]benzoic acid, 2-Butyl-5-[[5-{5H-Dibenzo[a,d]cyclohepten-5-yl}-3,4-dihydro-2-oxo-4-thioxo-1(2H)-pyrimidinyl]methyl] benzoic acid, 4-[5-{5H-Dibenzo[a,d]cyclohepten-5-yl}-3,4-dihydro-2-oxo-4-thioxo-1(2H)-pyrimidinyl]benzoic acid, 5-[[5-{5H-Dibenzo[a,d]cyclohepten-5-yl}-3,4-dihydro-2-oxo-4-thioxo-1(2H)-pyrimidinyl]methyl]phenyl-1,3-bis[oxyacetic acid], 4-[3-[Carboxymethoxy]-5-[[5-{5H-Dibenzo[a,d] cyclohepten-5-yl}-3,4-dihydro-2-oxo-4-thioxo-1(2H)-pyrimidinyl]methyl]phenyl]oxybutanoic aid, 3-[[3-[[5-{5-Dibenzo[a,d]cyclohepten-5-yl}-3,4-dihydro-2-oxo-4-thioxo-1(2H)-pyrimidinyl]methyl] phenyl][carboxymethyl]amino]-3-thioxobutanoic acid, N-[[3-[[5-{5-Dibenzo[a,d]cyclohepten-5-yl}-3,4-dihydro-2-oxo-4-thioxo-1(2H)-pyrimidinyl]methyl] phenyl]methyl]-N-[phenylmethoxycarbonyl]glycine, 3-[[5-{5-Dibenzo[a,d]cyclohepten-5-yl}-3,4-dihydro-2-oxo-4-thioxo-1(2H)-pyrimidinyl]methyl]-5-[[carboxymethyl][diphenylmethyl]amino]benzoic acid, 3-[[5-{5-Dibenzo[a,d]cyclohepten-5-yl}-3,4-dihydro-2-oxo-4-thioxo-1(2H)-pyrimidinyl]methyl]-5-[carboxymethylamino]benzoic acid 2-[2-[5-{5-Dibenzo[a,d]cyclohepten-5-yl}-3,4-dihydro-2-oxo-4-thioxo-1(2H)-pyrimidinyl]ethoxy]benzoic acid, 2-[Carboxymethoxy]-[6-[2-[5-{5-Dibenzo[a,d]cyclohepten-5-yl}-3,4-dihydro-2-oxo-4-thioxo-1(2H)-pyrimidinyl]ethoxy]benzoic acid, 4-[2-[5-{5-Dibenzo[a,d]cyclohepten-5-yl}-3,4-dihydro-2-oxo-4-thioxo-1(2H)-pyrimidinyl]ethoxy]-benzenedioic acid, 3-[[5-{5-Dibenzo[a,d]cyclohepten-5-yl}-3,4-dihydro-2-oxo-4-thioxo-1(2H)-pyrimidinyl]methyl]benzoic acid, 3-[[5-{5-Dibenzo[a,d]cyclohepten-5-yl}-3,4-dihydro-2-oxo-4-thioxo-1(2H)-pyrimidinyl]methyl]benzoic acid, or a pharmaceutically acceptable salt thereof.

8. A pharmaceutical composition comprising a compound of formula I or a salt or solvate thereof as defined in claim 1 in association with a pharmaceutically acceptable adjuvant, diluent or carrier.

9. A process for the preparation of compounds of formula I as defined in claim 1 which comprises: reacting a compound of formula (II):

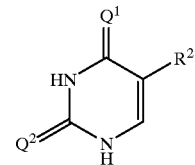

(II)

where $Q^1$, $Q^2$ and $R^2$ are defined in formula (I) or are protected derivatives thereof with a compound of formula (III):

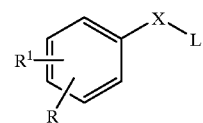

(III)

where R, $R^1$ and X are defined in formula (I) or are protected derivatives thereof and L is a leaving group, and optionally thereafter in any order:
  removing any protecting groups
  forming a salt.

10. A method of treating an inflammatory condition, which comprises the step of administering to a patient in need of such treatment an effective amount of a compound of formula (I) as defined in claim 1.

11. A method according to claim 10, wherein said compound of formula (I) is co-administered with another anti-inflammatory agent.

* * * * *